US007850973B2

(12) United States Patent
Garsky et al.

(10) Patent No.: US 7,850,973 B2
(45) Date of Patent: Dec. 14, 2010

(54) PEPTIDE CONJUGATE COMPOSITIONS AND METHODS FOR THE PREVENTION AND TREATMENT OF ALZHEIMER'S DISEASE

(75) Inventors: Victor M. Garsky, Blue Bell, PA (US); Joseph G. Joyce, Lansdale, PA (US); Paul M. Keller, Lansdale, PA (US); Gene Kinney, Collegeville, PA (US); Xiaoping Liang, Collegeville, PA (US); John W. Shiver, Doylestown, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 197 days.

(21) Appl. No.: 11/919,897

(22) PCT Filed: May 1, 2006

(86) PCT No.: PCT/US2006/016481

§ 371 (c)(1),
(2), (4) Date: Nov. 5, 2007

(87) PCT Pub. No.: WO2006/121656

PCT Pub. Date: Nov. 16, 2006

(65) Prior Publication Data

US 2009/0098155 A1 Apr. 16, 2009

Related U.S. Application Data

(60) Provisional application No. 60/677,886, filed on May 5, 2005.

(51) Int. Cl.
A61K 39/00 (2006.01)
A61K 39/08 (2006.01)
A61K 39/095 (2006.01)
A61K 39/02 (2006.01)
A61K 38/08 (2006.01)
A61K 45/00 (2006.01)
A61K 33/06 (2006.01)

(52) U.S. Cl. .............................. 424/185.1; 424/197.11; 424/236.1; 424/247.1; 424/250.1; 424/182.1; 424/682; 424/698; 424/278.1; 424/282.1; 424/283.1

(58) Field of Classification Search ........................ None
See application file for complete search history.

(56) References Cited

U.S. PATENT DOCUMENTS

| 6,743,427 | B1* | 6/2004 | Schenk ................. 424/130.1 |
| 6,787,144 | B1 | 9/2004 | Schenk |
| 6,808,712 | B2 | 10/2004 | Schenk |
| 2003/0157117 | A1* | 8/2003 | Rasmussen et al. ....... 424/185.1 |
| 2005/0053575 | A1* | 3/2005 | Solomon ................. 424/78.27 |
| 2007/0134762 | A1* | 6/2007 | Arumugham et al. ....... 435/69.1 |

FOREIGN PATENT DOCUMENTS

WO    WO 00/72880 A2 * 12/2000

WO    2004069182 A2    8/2004

OTHER PUBLICATIONS

Cribbs, et al., "Adjuvant-dependent modulation of Th1 and Th2 responses to immunization with Beta-amyloid," International Immunology, vol. 15, No. 4, 2003, pp. 505-514.
Agadjanyan, et al., "Prototype Alzheimer's Disease Vaccine Using the Immunodominant B Cell Epitope from Beta-Amyloid Promiscuous T Cell Epitope Pan HLA DR-Binding Peptide," Journal of Immunology, vol. 174, No. 3, 2005, pp. 1580-1586.
Bacskai, et al., Non-Fc-Mediated Mechanisms Are Involved in Clearance of Amyloid-B in Vivo by Immunotherapy,: The Journal of Neuroscience, Sep. 15, 2002, vol. 22, No. 18, pp. 7873-7878.
Bard, et al., "Peripherally administered antibodies against amyloid B-peptide enter the central nervous system and reduce pathology in a mouse model of Alzheimer disease," Nature Medicine, vol. 6, No. 8, Aug. 2000, pp. 916-919.
Davis, et al., "Deficient cerebral clearance of vasculotropic mutant Dutch/Iowa Double AB in human ABPP transgenic mice," Neurobiology of Aging, vol. 27, 2006, pp. 946-954.
Deane, et al., "AgG—Assisted Age-Dependent Clearance of Alzheimer's Amyloid B Peptide by the Blood-Brain Barrier Neonatal Fc Receptor", The Journal of Neuroscience, Dec. 14, 2005, vol. 25, No. 50, pp. 11495-11503.
DeMattos, et al., "Peripheral anti-AB antibody alters CNS and plasma AB clearance and decreases brain AB burden in a mouse model of Alzheimer's disease," PNAS, vol. 98, No. 15, Jul. 17, 2001, pp. 8850-8555.
Ferrer, et al., "Neuropathology and Pathogenesis of Encephalitis Following Amyloid-B Immunization in Alzheimer's Disease," Brain Pathology, vol., 14, 2004, pp. 11-20.
Gilman, et al., "Clinical effects of AB immunization (AN1792) in patients with AD in an interrupted trial," Neurology, vol. 64, May 2005, pp. 1553-1562.
Janus, et al., "AB peptide immunization reduces behavioural impairment and plaques in a model of Alzheimer's disease," Letters to Nature, vol. 408, Dec. 2000, pp. 979-982.
Lee, et al., "AB immunization: Moving AB peptide from brain to blood," PNAS, Jul. 31, 2001, vol. 98, No. 16, pp. 8931-8932.

(Continued)

Primary Examiner—Daniel E Kolker
Assistant Examiner—Kimberly A. Ballard
(74) Attorney, Agent, or Firm—Gerard Devlin; Joan E. Switzer

(57) ABSTRACT

The invention provides compositions and methods for the treatment of diseases associated with amyloid deposits of Aβ in the brain of a patient, such as Alzheimer's disease. Such methods entail administering an immunogenic fragment of Aβ, lacking a T-cell epitope, capable of inducing a beneficial immune response in the form of antibodies to Aβ. In another aspect, the immunogenic fragment of Aβ is capable of elevating plasma Aβ levels. The immunogenic fragments comprise linear or multivalent peptides of Aβ. Pharmaceutical compositions comprise the immunogenic fragment chemically linked to a carrier molecule which may be administered with an adjuvant.

10 Claims, 10 Drawing Sheets

OTHER PUBLICATIONS

Mesliah, et al., "AB vaccination effects on plaque pathology in the absence of encephalitis in Alzheimer disease," Neurology, vol. 64, Jan. 2005, pp. 129-131.

Monsonego, et al., "Increased T cell reactivity to amyloid B protein in older humans and patients with Alzheimer disease," J. Journal of Clinical Investigation, Aug. 2003, vol. 112, No. 3, pp. 415-422.

Morgan, et al., AB peptide vaccination prevents memory loss in an animal model of Alzheimer's disease, Nature, vol. 48, Dec. 2000, pp. 982-985.

Nicoll, et al., "Neuropathology of human Alzheimer disease after immunization with amyloid-B peptide: a case report," Nature Medicine, vol. 9, No. 4, Apr. 2003, pp. 448-452.

Orgogozo, et al., "Subacute meningoencephalitis in a subset of patients with AD after AB42 immunization," Neurology, vol. 61, Jul. 2003, pp. 46-54.

Schenk, et al., "Immunization with amyloid-B attenuates Alzheimer-diesase-like pathology in the PDAPP mouse," Letters to Nature, vol. 400, Jul. 8, 199, pp. 173-177.

Senior, "Drug with potential to clear amyloid," The Lancet Neurology, vol. 1, Jul. 2002, p. 142.

Wilcock, et al., "Intracranially Administered Anti-AB Antibodies Reduce B-Amyloid Deposition by Mechanisms Both Independent of and Associated with Microglial Activation," Journal of Neuroscience, vol. 23, No. 9, 2003, pp. 3745-3751.

* cited by examiner

| | |
|---|---|
| DAEFRHDSGYEVHHQKLVFFAEDVGSNKGAIIGLMVGGVVIA | SEQ ID NO:1 |
| DAEFRHDS | SEQ ID NO:2 |
| AEFRHDSG | SEQ ID NO:3 |
| EFRHDSGY | SEQ ID NO:4 |
| FRHDSGYE | SEQ ID NO:5 |
| RHDSGYEV | SEQ ID NO:6 |
| HDSGYEVH | SEQ ID NO:7 |
| DSGYEVHH | SEQ ID NO:8 |
| SGYEVHHQ | SEQ ID NO:9 |
| GYEVHHQK | SEQ ID NO:10 |
| YEVHHQKL | SEQ ID NO:11 |
| EVHHQKLV | SEQ ID NO:12 |
| VHHQKLVF | SEQ ID NO:13 |
| HHQKLVFF | SEQ ID NO:14 |
| HQKLVFFA | SEQ ID NO:15 |
| QKLVFFAE | SEQ ID NO:16 |
| KLVFFAED | SEQ ID NO:17 |
| LVFFAEDV | SEQ ID NO:18 |
| VFFAEDVG | SEQ ID NO:19 |
| FFAEDVGS | SEQ ID NO:20 |
| FAEDVGSN | SEQ ID NO:21 |
| AEDVGSNK | SEQ ID NO:22 |
| EDVGSNKG | SEQ ID NO:23 |
| DVGSNKGA | SEQ ID NO:24 |
| VGSNKGAI | SEQ ID NO:25 |
| GSNKGAII | SEQ ID NO:26 |
| SNKGAIIG | SEQ ID NO:27 |
| NKGAIIGL | SEQ ID NO:28 |
| KGAIIGLM | SEQ ID NO:29 |
| GAIIGLMV | SEQ ID NO:30 |
| AIIGLMVG | SEQ ID NO:31 |
| IIGLMVGG | SEQ ID NO:32 |
| IGLMVGGV | SEQ ID NO:33 |
| GLMVGGVV | SEQ ID NO:34 |
| LMVGGVVI | SEQ ID NO:35 |
| MVGGVVIA | SEQ ID NO:36 |

FIG. 1

| Peptide Scanning | Aβ position | Seq ID No. |
|---|---|---|
| 5 (Ac-DAEFRHDSGYEVHHQKLV-(Aha)-C-NH$_2$) | 1-18 | 37 |
| (Ac-DAEFRHDS-(Aha)-C-NH$_2$) | 1-8 | 38 |
| (Ac-AEFRHDSG-(Aha)-C-NH$_2$) | 2-9 | 39 |
| (Ac-EFRHDSGY-(Aha)-C-NH$_2$) | 3-10 | 40 |
| (Ac-FRHDSGYE-(Aha)-C-NH$_2$) | 4-11 | 41 |
| 10 (Ac-RHDSGYEV-(Aha)-C-NH$_2$) | 5-12 | 42 |
| (Ac-HDSGYEVH-(Aha)-C-NH$_2$) | 6-13 | 43 |
| (Ac-DSGYEVHH-(Aha)-C-NH$_2$) | 7-14 | 44 |
| (Ac-SGYEVHHQ-(Aha)-C-NH$_2$) | 8-15 | 45 |
| (Ac-GYEVHHQK-(Aha)-C-NH$_2$) | 9-16 | 46 |
| 15 (Ac-YEVHHQKL-(Aha)-C-NH$_2$) | 10-17 | 47 |
| (Ac-EVHHQKLV-(Aha)-C-NH$_2$) | 11-18 | 48 |
| (Ac-HHQKLVFF-(Aha)-C-NH$_2$) | 13-20 | 49 |
| (Ac-EVHHQKLVEEE-(Aha)-C-NH$_2$) | 11-18 | 50 |
| (Ac-HHQKLVFFEEE-(Aha-C-NH$_2$) | 13-20 | 51 |
| 20 (Ac-HHQKLVFFKKK-(Aha-C-NH$_2$) | 13-20 | 52 |
| (Ac-QKLVFFAEKKK-(Aha-C-NH$_2$) | 15-22 | 53 |
| (Ac-LVFFAEDVKKK-(Aha-C-NH$_2$) | 17-24 | 54 |
| (Ac-LVFFAEDV-(PEG)-(Aha)-C-NH$_2$) | 17-24 | 55 |
| (Ac-FFAEDVGSKKK-(Aha)-C-NH$_2$) | 19-26 | 56 |
| 25 (Ac-AEDVGSNK-(Aha)-C-NH$_2$) | 21-28 | 57 |
| (Ac-DVGSNKGA-(Aha)-C-NH$_2$) | 23-30 | 58 |
| (Ac-GSNKGAIIKKK-(Aha)-C-NH) | 25-32 | 59 |
| (Ac-NKGAIIGLKKK-(Aha)-C-NH$_2$) | 27-34 | 60 |
| (Ac-GAIIGLMVEEE-(Aha)-C-NH$_2$) | 29-36 | 61 |
| 30 (Ac-IIGLMVGGKKK-(Aha)-C-NH$_2$) | 31-38 | 62 |
| (Ac-GLMVGGVV-(PEG)-(Aha)-C-NH$_2$) | 33-40 | 63 |
| (Ac-GLMVGGVVKKK-(Aha)-C-NH$_2$) | 33-40 | 64 |
| (Ac-MVGGVVIAKKK-(Aha)-C-NH$_2$) | 35-42 | 65 |

35 (PEG)= -NHCH$_2$CH$_2$O(CH$_2$CH$_2$O)$_6$CH$_2$CH$_2$NHCOCH$_2$OCH$_2$CO-
(Aha)= 6-aminohexanoic acid

FIG.2A

Aβ (1-8)   Ac-DAEFRHDS-(Aha)-K(BrAc)NH₂                       SEQ ID NO.67

Aβ (2-9)   Ac-AEFRHDSG-(Aha)-K(BrAc)NH₂                       SEQ ID NO.68

Aβ (3-10)  Ac-EFRHDSGY-(Aha)-K(BrAc)NH₂                       SEQ ID NO.69

Aβ (7-14)  Ac-DSGYEVHH-(Aha)-K(BrAc)NH₂                       SEQ ID NO.70

Aβ (8-15)  Ac-SGYEVHHQ-(Aha)-K(BrAc)NH₂                       SEQ ID NO.71

Aβ (17-24) Ac-LVFFAEDV-(PEG)-(Aha)-K(BrAc)NH₂                 SEQ ID NO.72

Aβ (21-28) Ac-AEDVGSNK-(Aha)-K(BrAc)NH₂                       SEQ ID NO.73

Aβ (33-40) Ac-GLMVGGVV-(PEG)-(Aha)-K-(BrAc)NH₂                SEQ ID NO.74

Aβ-EV (1-18) Ac-EVEFRHDSGYEVHHQKLV-(Aha)-K(BrAc)NH₂           SEQ ID NO.75

Aβ-EV (1-10) Ac-EVEFRHDSGY-(Aha)-K(BrAc)NH₂                   SEQ ID NO.76

Aβ-EV (1-8)  Ac-EVEFRHDS-(Aha)-K(BrAc)NH₂                     SEQ ID NO.77

(PEG)= $-NHCH_2CH_2O(CH_2CH_2O)_6CH_2CH_2NHCOCH_2OCH_2CO-$ (Aha)= 6-aminohexanoic acid

FIG.2B

| Aβ amino acid # | Construct | SEQ ID No. | PD1 | PD2 | PD3 |
|---|---|---|---|---|---|
| 1-18 | Ac-DAEFRHDSGYEVHHQKLV-(Aha)-C-NH2 | 37 | 3200 | 102400 | 102400 |
| 1-8 | Ac-DAEFRHDS-(Aha)-C-NH2 | 38 | 1600 | 51200 | 102400 |
| 2-9 | Ac-AEFRHDSG-(Aha)-C-NH2 | 39 | 1600 | 3200 | 1600 |
| 3-10 | Ac-EFRHDSGY-(Aha)-C-NH2 | 40 | 3200 | 25600 | 6400 |
| 4-11 | Ac-FRHDSGYE-(Aha)-C-NH2 | 41 | 100 | 100 | 1600 |
| 5-12 | Ac-RHDSGYEV-(Aha)-C-NH2 | 42 | 100 | 100 | 200 |
| 6-13 | Ac-HDSGYEVH-(Aha)-C-NH2 | 43 | 100 | 400 | 3200 |
| 7-14 | Ac-DSGYEVHH-(Aha)-C-NH2 | 44 | 400 | 1600 | 6400 |
| 8-15 | Ac-SGYEVHHQ-(Aha)-C-NH2 | 45 | 200 | 800 | 3200 |
| 9-16 | Ac-GYEVHHQK-(Aha)-C-NH2 | 46 | 100 | 400 | 1600 |
| 10-17 | Ac-YEVHHQKL-(Aha)-C-NH2 | 47 | 100 | 3200 | 1600 |
| 11-18 | Ac-EVHHQKLV-(Aha)-C-NH2 | 48 | 200 | 800 | 400 |
| 13-20 | Ac-HHQKLVFF-(Aha)-C-NH2 | 49 | 200 | 1600 | 6400 |
| 11-18 | Ac-EVHHQKLVEEE-(Aha)-C-NH2 | 50 | 100 | 6400 | 6400 |
| 13-20 | Ac-HHQKLVFFEEE-(Aha)-C-NH2 | 51 | 100 | 1600 | 6406.25 |
| 13-20 | Ac-HHQKLVFFKKK-(Aha)-C-NH2 | 52 | 100 | 100 | 200 |
| 15-22 | Ac-QKLVFFAEKKK-(Aha)-C-NH2 | 53 | 400 | 6400 | 25600 |
| 17-24 | Ac-LVFFAEDVKKK-(Aha)-C-NH2 | 54 | 800 | 400 | 800 |
| 17-24 | Ac-LVFFAEDV-(PEG)-(Aha)-C-NH2 | 55 | 1600 | 800 | 400 |
| 19-26 | Ac-FFAEDVGSKKK-(Aha)-C-NH2 | 56 | 100 | 1600 | 6400 |
| 21-28 | Ac-AEDVGSNK-(Aha)-C-NH2 | 57 | 3200 | 102400 | 51200 |
| 23-30 | Ac-DVGSNKGA-(Aha)-C-NH2 | 58 | 400 | 25600 | 25600 |
| 25-32 | Ac-GSNKGAIIKKK-(Aha)-C-NH | 59 | 100 | 100 | 100 |
| 27-34 | Ac-NKGAIIGLKKK-(Aha)-C-NH2 | 60 | 100 | 6400 | 6400 |
| 29-36 | Ac-GAIIGLMVEEE-(Aha)-C-NH2 | 61 | 100 | 6400 | 12800 |
| 31-38 | Ac-IIGLMVGGKKK-(Aha)-C-NH2 | 62 | 100 | 100 | 100 |
| 33-40 | Ac-GLMVGGVV-(PEG)-(Aha)-C-NH2 | 63 | 800 | 1600 | 3200 |
| 33-40 | Ac-GLMVGGVVKKK-(Aha)-C-NH2 | 64 | 400 | 800 | 400 |
| 35-42 | Ac-MVGGVVIAKKK-(Aha)-C-NH2 | 65 | 100 | 100 | 100 |

FIG.3

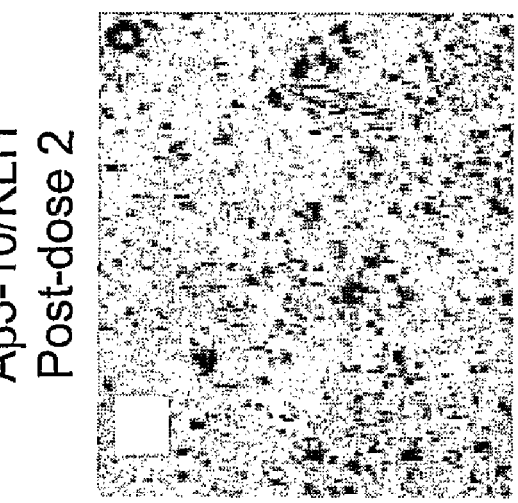
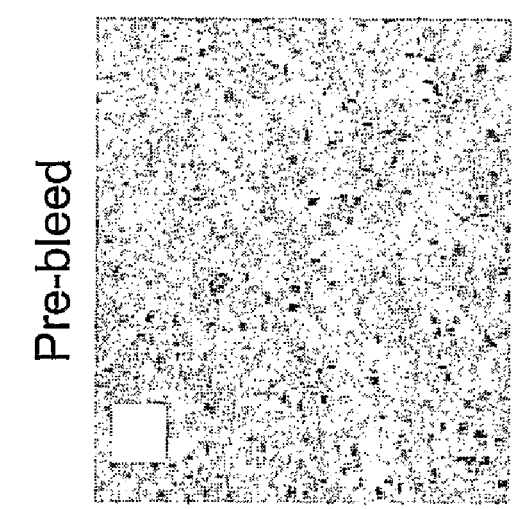
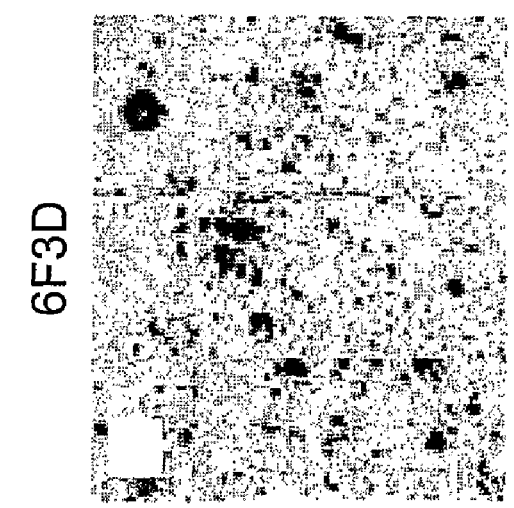
FIG. 4C
FIG. 4B
FIG. 4A

*1. BrAc-Aha-(PEG)-DSGYEVHH-(PEG)-EFRHDSGY-NH$_2$

*2. BrAc-Aha-(PEG)-AEDVGSNK-(PEG)-EFRHDSGY-NH$_2$

*3. BrAc-Aha-(PEG)-LVFFAEDV-(PEG)-EFRHDSGY-NH$_2$

*4. BrAc-Aha-(PEG)-GLMVGGV-(PEG)-EFRHDSGY-NH$_2$

*5. BrAc-Aha-(PEG)-AEDVGSNK-(PEG)-DAEFRHDS-NH$_2$

*6. BrAc-Aha-(PEG)-AEDVGSNK-(PEG)-DSGYEVHH-(PEG)-EFRHDSGY-NH$_2$

*7. BrAc-Aha-(PEG)-AEDVGSNK-(PEG)-AEFRHDSG-(PEG)-EFRHDSGY-(PEG)-DAEFRHDS-NH$_2$

\* Also Cys derivative for conjugation to KLH / guinea pig (PEG)= -NHCH$_2$CH$_2$O(CH$_2$CH$_2$O)$_6$CH$_2$CH$_2$NHCOCH$_2$OCH$_2$CO- (Aha)= 6-aminohexanoic acid (BrAc)= Bromoacetyl

FIG.5

8. Aβ (3–10)   Ac–EFRHDSGY(Aha)–Lys–Lys(BrAc)–NH₂
   Aβ (7–14)   Ac–DSGYEVHH(Aha)⏋

9. Aβ (3–10)   Ac–EFRHDSGY(Aha)–Lys–Cys–NH₂
   Aβ (7–14)   Ac–DSGYEVHH(Aha)⏋

10. Aβ (3–10)  Ac–EFRHDSGY(Aha)–Lys–Cys–NH₂
    Aβ (17–24) Ac–LVFFAEDV(PEG)⏋

11. Aβ (1–8)   Ac–DAEFRHDS(Aha)–Lys–Lys(BrAc)–NH₂
    Aβ (21–28) Ac–AEDVGSNK(Aha)⏋

12. Aβ (3–10)  Ac–EFRHDSGY(Aha)–Lys–Lys(BrAc)–NH₂
    Aβ (21–28) Ac–AEDVGSNK(Aha)⏋

13. Aβ (3–10)  Ac–EFRHDSGY(Aha)–Lys–Cys–NH₂
    Aβ (21–28) Ac–AEDVGSNK(Aha)⏋

14. Aβ (3–10)  Ac–EFRHDSGY(Aha)–Lys–Cys–NH₂
    Aβ (33–40) Ac–GLMVGGVV(PEG)⏋

Cys or Lys(BrAc) as functionalized linkers for conjugation
(PEG)= $-NHCH_2CH_2O(CH_2CH_2O)_6CH_2CH_2NHCOCH_2OCH_2CO-$
(Aha)= 6-aminohexanoic acid

FIG.6A

*15. Aβ(7-14)      Ac-DSGYEVHH-(Aha)-NᵋH
                                    |
                                    BrAc-Lys-Lys-Lys-NH₂
    Aβ(21-28)     Ac-AEDVGSNK-(Aha)-NᵋH       |
    Aβ(3-10)           Ac-EFRHDSGY-(Aha)-NᵋH

*16. Aβ(7-14)      Ac-DSGYEVHH-(Aha)-NᵋH
    Aβ(33-40)  Ac-GLMVGGVV-(Aha)-NᵋH          |
                                    |
                                    BrAc-Lys-Lys-Lys-Lys-NH₂
    Aβ(21-28)     Ac-AEDVGSNK-(Aha)-NᵋH       |
    Aβ(3-10)           Ac-EFRHDSGY-(Aha)-NᵋH

17. Aβ(7-14)      Ac-DSGYEVHH(Aha)-NᵋH
                                 |
    Aβ(3-10)      Ac-EFRHDSGY(Aha)-Lys-Lys-Cys-NH₂
                                      |
    Aβ(3-10)      Ac-EFRHDSGY(Aha)-Lys-NᵋH
                                      |
    Aβ(7-14)      Ac-DSGYEVHH(Aha)-NᵋH

\*
Also Cys derivative for conjugation to KLH
(Aha)= 6-aminohexanoic acid
(BrAc)= Bromoacetyl

FIG.6B

SEQUENCE LISTING

```
<160> NUMBER OF SEQ ID NOS: 79

<210> SEQ ID NO 1
<211> LENGTH: 42
<212> TYPE: PRT
<213> ORGANISM: Artificial Sequence
<220> FEATURE:
<223> OTHER INFORMATION: Synthetic Peptide

<400> SEQUENCE: 1

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 2

Asp Ala Glu Phe Arg His Asp Ser
 1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 3

Ala Glu Phe Arg His Asp Ser Gly
 1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 4

Glu Phe Arg His Asp Ser Gly Tyr
 1               5
```

```
<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 5

Phe Arg His Asp Ser Gly Tyr Glu
 1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 6

Arg His Asp Ser Gly Tyr Glu Val
 1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 7

His Asp Ser Gly Tyr Glu Val His
 1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 8

Asp Ser Gly Tyr Glu Val His His
 1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 9

Ser Gly Tyr Glu Val His His Gln
 1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 10

Gly Tyr Glu Val His His Gln Lys
 1               5
```

```
<210> SEQ ID NO 11
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 11

Tyr Glu Val His His Gln Lys Leu
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 12

Glu Val His His Gln Lys Leu Val
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 13

Val His His Gln Lys Leu Val Phe
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 14

His His Gln Lys Leu Val Phe Phe
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 15

His Gln Lys Leu Val Phe Phe Ala
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 16

Gln Lys Leu Val Phe Phe Ala Glu
1               5

<210> SEQ ID NO 17
```

```
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 17

Lys Leu Val Phe Phe Ala Glu Asp
 1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 18

Leu Val Phe Phe Ala Glu Asp Val
 1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 19

Val Phe Phe Ala Glu Asp Val Gly
 1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 20

Phe Phe Ala Glu Asp Val Gly Ser
 1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 21

Phe Ala Glu Asp Val Gly Ser Asn
 1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 22

Ala Glu Asp Val Gly Ser Asn Lys
 1               5

<210> SEQ ID NO 23
<211> LENGTH: 8
```

```
<212> TYPE: PRT
<213> ORGANISM: Artificial Sequence
<220> FEATURE:
<223> OTHER INFORMATION: Synthetic Peptide

<400> SEQUENCE: 23

Glu Asp Val Gly Ser Asn Lys Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 24

Asp Val Gly Ser Asn Lys Gly Ala
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 25

Val Gly Ser Asn Lys Gly Ala Ile
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 26

Gly Ser Asn Lys Gly Ala Ile Ile
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 27

Ser Asn Lys Gly Ala Ile Ile Gly
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 28

Asn Lys Gly Ala Ile Ile Gly Leu
1               5

<210> SEQ ID NO 29
<211> LENGTH: 8
<212> TYPE: PRT
```

<213> ORGANISM: Artificial Sequence
<220> FEATURE:
<223> OTHER INFORMATION: Synthetic Peptide

<400> SEQUENCE: 29

Lys Gly Ala Ile Ile Gly Leu Met
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 30

Gly Ala Ile Ile Gly Leu Met Val
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 31

Ala Ile Ile Gly Leu Met Val Gly
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 32

Ile Ile Gly Leu Met Val Gly Gly
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 33

Ile Gly Leu Met Val Gly Gly Val
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 34

Gly Leu Met Val Gly Gly Val Val
1               5

<210> SEQ ID NO 35
<211> LENGTH: 8
<212> TYPE: PRT
<213> ORGANISM: Artificial Sequence

```
<220> FEATURE:
<223> OTHER INFORMATION: Synthetic Peptide

<400> SEQUENCE: 35

Leu Met Val Gly Gly Val Val Ile
 1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 36

Met Val Gly Gly Val Val Ile Ala
 1               5

<210> SEQ ID NO 37
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 37

Asp Ala Glu Phe Arg His Asp Ser Gly Tyr Glu Val His His Gln Lys
 1               5                  10                  15

Leu Val

<210> SEQ ID NO 38
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 38

Asp Ala Glu Phe Arg His Asp Ser
 1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 39

Ala Glu Phe Arg His Asp Ser Gly
 1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 40

Glu Phe Arg His Asp Ser Gly Tyr
 1               5

<210> SEQ ID NO 41
<211> LENGTH: 8
<212> TYPE: PRT
```

```
<213> ORGANISM: Artificial Sequence
<220> FEATURE:
<223> OTHER INFORMATION: Synthetic Peptide

<400> SEQUENCE: 41

Phe Arg His Asp Ser Gly Tyr Glu
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 42

Arg His Asp Ser Gly Tyr Glu Val
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 43

His Asp Ser Gly Tyr Glu Val His
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 44

Asp Ser Gly Tyr Glu Val His His
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 45

Ser Gly Tyr Glu Val His His Gln
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 46

Gly Tyr Glu Val His His Gln Lys
1               5

<210> SEQ ID NO 47
<211> LENGTH: 8
<212> TYPE: PRT
<213> ORGANISM: Artificial Sequence
```

```
<220> FEATURE:
<223> OTHER INFORMATION: Synthetic Peptide

<400> SEQUENCE: 47

Tyr Glu Val His His Gln Lys Leu
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 48

Glu Val His His Gln Lys Leu Val
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 49

His His Gln Lys Leu Val Phe Phe
1               5

<210> SEQ ID NO 50
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 50

Glu Val His His Gln Lys Leu Val Glu Glu Glu
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 51

His His Gln Lys Leu Val Phe Phe Glu Glu Glu
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 52

His His Gln Lys Leu Val Phe Phe Lys Lys Lys
1               5                   10

<210> SEQ ID NO 53
<211> LENGTH: 11
<212> TYPE: PRT
<213> ORGANISM: Artificial Sequence
<220> FEATURE:
```

-continued

<223> OTHER INFORMATION: Synthetic Peptide

<400> SEQUENCE: 53

Gln Lys Leu Val Phe Phe Ala Glu Lys Lys
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 54

Leu Val Phe Phe Ala Glu Asp Val Lys Lys
1               5                   10

<210> SEQ ID NO 55
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 55

Leu Val Phe Phe Ala Glu Asp Val
1               5

<210> SEQ ID NO 56
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 56

Phe Phe Ala Glu Asp Val Gly Ser Lys Lys
1               5                   10

<210> SEQ ID NO 57
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 57

Ala Glu Asp Val Gly Ser Asn Lys
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 58

Asp Val Gly Ser Asn Lys Gly Ala
1               5

<210> SEQ ID NO 59
<211> LENGTH: 11
<212> TYPE: PRT
<213> ORGANISM: Artificial Sequence
<220> FEATURE:
<223> OTHER INFORMATION: Synthetic Peptide

```
<400> SEQUENCE: 59

Gly Ser Asn Lys Gly Ala Ile Ile Lys Lys Lys
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 60

Asn Lys Gly Ala Ile Ile Gly Leu Lys Lys Lys
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 61

Gly Ala Ile Ile Gly Leu Met Val Glu Glu Glu
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 62

Ile Ile Gly Leu Met Val Gly Gly Lys Lys Lys
1               5                   10

<210> SEQ ID NO 63
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 63

Gly Leu Met Val Gly Gly Val Val
1               5

<210> SEQ ID NO 64
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 64

Gly Leu Met Val Gly Gly Val Val Lys Lys Lys
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic Peptide
```

```
<400> SEQUENCE: 65

Met Val Gly Gly Val Val Ile Ala Lys Lys Lys
1               5                   10

<210> SEQ ID NO 66
<211> LENGTH: 42
<212> TYPE: PRT
<213> ORGANISM: Artificial Sequence
<220> FEATURE:
<223> OTHER INFORMATION: Synthetic Peptide

<400> SEQUENCE: 66

Glu Val Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 67
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 67

Asp Ala Glu Phe Arg His Asp Ser
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 68

Ala Glu Phe Arg His Asp Ser Gly
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 69

Glu Phe Arg His Asp Ser Gly Tyr
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 70

Asp Ser Gly Tyr Glu Val His His
1               5

<210> SEQ ID NO 71
<211> LENGTH: 8
```

<212> TYPE: PRT
<213> ORGANISM: Artificial Sequence
<220> FEATURE:
<223> OTHER INFORMATION: Synthetic Peptide

<400> SEQUENCE: 71

Ser Gly Tyr Glu Val His His Gln
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 72

Leu Val Phe Phe Ala Glu Asp Val
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 73

Ala Glu Asp Val Gly Ser Asn Lys
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 74

Gly Leu Met Val Gly Gly Val Val
1               5

<210> SEQ ID NO 75
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 75

Glu Val Glu Phe Arg His Asp Ser Gly Tyr Glu Val His His Gln Lys
1               5                   10                  15

Leu Val

<210> SEQ ID NO 76
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 76

Glu Val Glu Phe Arg His Asp Ser Gly Tyr
1               5                   10

<210> SEQ ID NO 77

```
-continued

<211> LENGTH: 8
<212> TYPE: PRT
<213> ORGANISM: Artificial Sequence
<220> FEATURE:
<223> OTHER INFORMATION: Synthetic Peptide

<400> SEQUENCE: 77

Glu Val Glu Phe Arg His Asp Ser
 1               5

<210> SEQ ID NO 78
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 78

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
             20                  25                  30

Gly Leu Met Val Gly Gly Val Val
         35                  40

<210> SEQ ID NO 79
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 79

Asp Ala Glu Phe Arg His Asp Ser Gly Tyr Glu Val His His Gln Lys
 1               5                  10                  15

Leu Val Phe Phe
             20
```

PEPTIDE CONJUGATE COMPOSITIONS AND METHODS FOR THE PREVENTION AND TREATMENT OF ALZHEIMER'S DISEASE

CROSS REFERENCE TO RELATED APPLICATIONS

This application is a U.S. national application of PCT/US2006/016481, filed May 1, 2006 and which published as WO 2006/121656, Nov. 16, 2006, and which claims the benefit of U.S. Provisional Patent Application No. 60/677,886, filed May 5, 2005.

FIELD OF THE INVENTION

The present invention relates to compositions and methods for the prevention and treatment of amyloidogenic diseases and, in particular, Alzheimer's disease.

BACKGROUND OF THE INVENTION

Alzheimer's disease (AD) is characterized by progressive memory impairment and cognitive decline. Its hallmark pathological lesions are amyloid deposits (senile plaques), neurofibrillary tangles and neuronal loss in specific brain regions. The amyloid deposits are composed of amyloid beta peptides (Aβ) of 40 to 43 amino acid residues, which are the proteolytic products of the amyloid precursor protein (APP). Neurofibrillary tangles are the intracellular filamentous aggregates of hyperphosphorylated tau proteins (Selkoe, *Science*, 275: 630-631, 1997).

The pathogenesis of AD has not been fully understood, but it is expected to be a multi-factored event. Accumulation and aggregation of Aβ in brain tissue is believed to play a pivotal role in the disease process, also know as the amyloid cascade hypothesis (Golde, *Brain Pathol.*, 15: 84-87, 1995). According to this hypothesis, Aβ, particularly $A\beta_{42}$, is prone to form various forms of aggregates, ranging from small oligomers to large, elongated profibrile structures. These aggregates are neurotoxic and are responsible for the synaptic pathology associated with the memory loss and cognition decline in the early stage of the disease (Klein et al., *Neurobiol. Aging*, 25: 569-580, 2004). A recent publication suggests that reduction of Aβ in a triple transgenic mouse model also prevents intracellular tau deposition (Oddo et al., Proc. *Neuron*, 43:321-332, 2004). This finding suggests that the extracellular amyloid deposition may be causative for subsequent neurofibrillary tangle formation, which may in turn lead to neuronal loss.

Immunization of APP transgenic mice with Aβ antigen can reduce the brain Aβ deposits and mitigate disease progression. This was first reported by Shenk et al., *Nature*, 400: 173-177, 1999, and has now been corroborated by a large number of studies involving different transgenic animal models, various active vaccines as well as passive immunization with Aβ specific monoclonal antibodies (Bard et al., *Nature Med*, 6: 916-919, 2000; Janus et al., *Nature*, 408: 979-982, 2000; Morgan et al., *Nature*, 408: 982-985, 2000; DeMattos et al., *Proc. Natl. Acad. Sci.*, 98: 8850-8855, 2001; Bacskai et al., *J. Neurosci.*, 22: 7873-7878, 2002; Wilcock et al., *J. Neurosci.*, 23: 3745-3751, 2003). Consistent with these animal data, three published evaluations of postmortem human brain tissues from patients who had previously received active immunization with a pre-aggregated Aβ (1-42) immunogen (AN1792, Betabloc) showed regional clearance of senile plaques (Nicoll et al., *Nature Med.*, 9: 448-452, 2003; Ferrer et al., *Brain Pathol.*, 14: 11-20, 2004; Masliah et al., *Neurology*, 64: 129-131, 2005). This data collectively indicates that vaccines that effectively elicit antibody responses to Aβ antigens are efficacious against the pathological senile plaques found in AD. However, the mechanism of vaccine or antibody efficacy remains to be defined.

The most advanced immunotherapy-based AD program in the public domain had been an active immunization Phase II vaccine trial using AN1792 (Betabloc), a vaccine composed of pre-aggregated Aβ (1-42) co-administered with the adjuvant, QS-21™ (Antigenics, New York, N.Y.). In January 2002, this study was terminated when four patients showed symptoms consistent with meningoencephalitis (Senior, *Lancet Neurol.*, 1: 3, 2002). Ultimately, 18 of 298 treated patients developed signs of meningoencephalitis (Orgogozo et al., *Neurology*, 61: 46-54, 2003). There was no correlation between encephalitis and antibody titer and it has been reported that the likely causative mechanism for this effect was activation of T-cells to the self-immunogen, particularly the mid- and carboxy-terminal portion of the $A\beta_{42}$ peptide (Monsonego et al., *J. Clin. Invest.*, 112: 415-422, 2003). In support of this conclusion, postmortem examination of brain tissues from two vaccine recipients that developed encephalitis revealed substantial meningeal infiltration of CD4+ T cells in one patient (Nicoll et al., *Nature Med.*, 9: 448-452, 2003) and CD4+, CD8+, CD3+, CD5+, CD7+ T cells in the other (Ferrer et al., *Brain Pathol.*, 14: 11-20, 2004).

Current evidence suggests that increases in plasma Aβ levels following passive or active immunization reflect the initiation of a peripheral sink as a precursor to subsequent decreases in brain Aβ. The peripheral sink refers to a change in the equilibrium of brain and plasma Aβ stores resulting in a net efflux of central Aβ to the periphery (see, for example, Deane et al., *J. Neurosci.*, 25: 11495-11503, 2005; DeMattos et al., *Pro. Natl. Acad. Sci. USA*, 98: 8931-8932, 2001). Other studies suggest that this increase in plasma Aβ observed following anti-Aβ immunotherapy is necessary for subsequent decreases in central Aβ to be realized (Cribbs et al., 7th International Conference on AD/PD, Sorrento, Italy, 2005). Thus, when two amino acids within Aβ are substituted (for example, such as occurs with the Dutch and Iowa mutations) the peptide is no longer able to cross from central to peripheral compartments (Davis et al., *Neurobiol. Aging*, in press, available on line 18 Aug. 2005). When mice expressing this mutant form of Aβ and the Swedish mutation were immunized, no elevations in plasma Aβ were found and no subsequent lowering of brain Aβ was noted. By contrast, mice expressing the wild-type human Aβ sequence plus the Swedish mutation responded to active immunization with both increases in plasma Aβ and subsequent decreases in central Aβ (Cribbs et al., 7th International Conference on AD/PD, Sorrento, Italy, 2005). Accordingly, it is expected that any active vaccine immunogen capable of generating an immune response that results in the elevation of plasma Aβ levels will be useful for the treatment of Alzheimer's disease and related disorders characterized by elevated brain Aβ levels.

Applicants herein have surprisingly found that an antigen which eliminated T-cell epitopes, to avoid a self T-cell response, is immunogenic and elevates plasma Aβ levels. This represents a potential means to produce a safe and effective AD vaccine. Applicants herein provide such an antigen and a formulation for use as an AD vaccine.

SUMMARY OF THE INVENTION

In one embodiment, the invention provides a pharmaceutical composition comprising an immunogenic fragment of Aβ, lacking a T-cell epitope, capable of inducing an immune response in the form of antibodies to Aβ. In one aspect, this composition comprises linear 8 amino acid peptides (8-mers) of Aβ. In still another aspect, this composition comprises multivalent linear 8-mers interspersed with at least one spacer or a multivalent branched multiple antigenic peptide (MAP). The pharmaceutical composition can be used as a vaccine for AD and related amyloid diseases.

In another embodiment of the invention, the pharmaceutical composition is an Aβ plasma elevating agent comprising an immunogenic fragment of Aβ, lacking a T-cell epitope, capable of inducing an immune response in the form of antibodies to Aβ that elevate plasma Aβ levels. The pharmaceutical composition can be used as a vaccine for AD and related amyloid diseases characterized by elevated brain Aβ levels.

In still another embodiment of the invention, the pharmaceutical composition is linked to a carrier molecule to form a conjugate, wherein the carrier helps to elicit an immune response comprising antibodies to the Aβ fragment. In a preferred embodiment of the invention, the carrier is the outer membrane protein complex of *Neisseria meningitides* (OMPC).

In a further embodiment of the invention, the pharmaceutical composition is administered with a pharmaceutically acceptable adjuvant. In a preferred embodiment the adjuvant is an aluminum adjuvant (Merck alum adjuvant, MAA) or a saponin-based adjuvant (ISCOMATRIX®, CSL Ltd., Parkville, Australia).

In still another embodiment, the invention provides methods for preventing or treating a disease associated with amyloid deposits of Aβ in the brain of a patient. Such diseases include Alzheimer's disease, Down's syndrome, cognitive impairment or other forms of senile dementia. The method comprises administering an immunogenic fragment of Aβ, lacking a T-cell epitope, selected from the group consisting of linear 8 amino acid peptides (8-mers), a multivalent linear peptides interspersed with at least one spacer and a multivalent branched multiple antigenic peptide (MAP). In a preferred embodiment the immunogenic fragment comprises a multivalent linear peptide with a polyethylene glycol (PEG) spacer. In a more preferred embodiment the immunogenic fragment comprises a multivalent branched MAP, Aβ (3-10)/(21-28) conjugate, Construct No. 12, FIG. 6A, conjugated to OMPC.

Such methods entail the administration of an effective dose of an immunogenic fragment of Aβ, lacking a T-cell epitope, to patients in need of such treatment that will induce an immune response in the form of antibodies to Aβ. Said antibody response is capable of elevating plasma Aβ levels. In another aspect of this embodiment, the immunogenic fragment to be administered is linked to a carrier molecule. In yet another aspect of this embodiment, the immunogenic fragment is administered with an adjuvant.

BRIEF DESCRIPTION OF THE DRAWINGS

FIG. 1 represents synthetic 8-amino acid peptides (8-mers) (SEQ ID NOS: 2-36) derived from Aβ (1-42) (SEQ ID NO: 1) from which peptides were selected to conduct a linear peptide scan to identify the epitopes of Aβ.

FIG. 2 represents the 8-mers selected for conjugation to KLH (FIG. 2A) and OMPC (FIG. 2B).

FIG. 3 represents the immunogenicity of selected Aβ conjugates, described in FIG. 2, after the first (PD1), second (PD2) and third dose (PD3).

FIG. 4 represents the cross-reactivity of sera extracted from a guinea pig previously immunized with an Aβ (3-10)-KLH conjugate (SEQ ID NO: 40) on human AD brain tissue.

FIG. 4A shows immunoreactivity of the anti-Aβ monoclonal antibody 6F3D (which recognizes amino acids 8-17 of Aβ). The staining pattern reveals extensive amyloid pathology in this human brain. FIG. 4B demonstrates a lack of immunoreactivity of this same brain to the pre-immune sera from the immunized guinea pig prior to immunization. FIG. 4C shows the immunoreactivity of the sera from an immunized guinea pig following immunization FIG. 5 shows representative multivalent linear 8-mer peptides, which were selected based on the immunogenicity of the separate 8-mers in guinea pig studies (Example 3). These conjugates were synthesized as described and conjugated to OMPC (Example 1.J and 1.K).

FIG. 6 shows representative multivalent branched MAP conjugates, which were selected based on the immunogenicity of the separate 8-mers in guinea pig studies (Example 3). FIG. 6A shows representative divalent MAPs and FIG. 6B shows representative bromoacetyl-cysteine MAPs. These conjugates were synthesized as described and conjugated to OMPC (Example 2).

FIG. 8 represents the increase in plasma Aβ levels following administration of a Aβ conjugate.

DEFINITIONS

Figure 7:
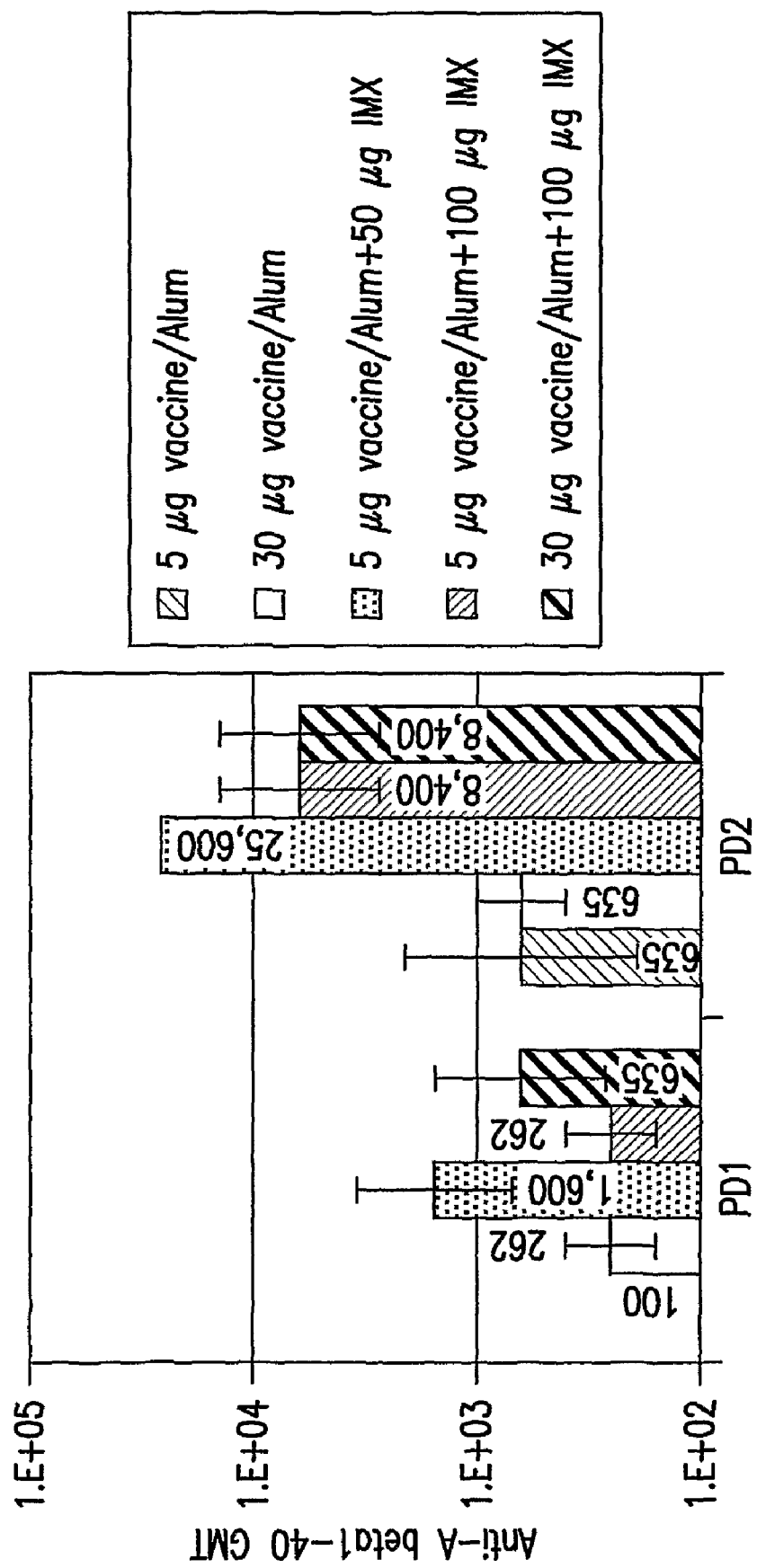
FIG. 7 represents the anti-Aβ$_{40}$ titer from sera collected from rhesus monkeys following 1 (PD1) or 2 (PD2) injections with an Aβ (1-18) peptide conjugated to OMPC formulated in Merck alum alone or Merck alum plus IMX (ISCOMATRIX®, CSL, Ltd., Parkville, Australia) as an adjuvant.

The term "8-mer" refers to an eight amino acid peptide which corresponds to a fragment of Aβ, an analog of a natural Aβ peptide or a peptide mimetic. One or more 8-mers may be combined with at least one spacer to form a multivalent linear peptide or to form a multivalent branched MAP.

The term "Aβ conjugate" means an 8-mer or immunogenic fragment of Aβ that is chemically or biologically linked to a carrier, such as keyhole limpet hemocyanin or the outer membrane protein complex of *Nesseria meningitidies* (OMPC).

The term "Aβ peptide" means any of the Aβ peptides described herein, including, but not limited to, linear 8-mers, multivalent linear peptides with at least one spacer and multivalent branched multiple antigenic peptides (MAPs).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. T-cell epitopes consist of peptides which are capable of forming complexes with host MHC molecules. T-cell epitopes for a human MHC class I molecules, which are responsible for induction of CD8+ T-cell responses, generally comprise 9 to 11 amino acid residues, while epitopes for human MHC class II molecules, which are responsible for CD4+ T-cell responses, typically comprise 12 or more amino acid residues (Bjorkman et al. *Nature* 329:506-512, 1987;

Madden et al. Cell 75:693-708; Batalia and Collins; Engelhard *Annu Rev Immunol.*, 12: 181-207-622. 1995; Madden, *Annu Rev Immunol.*, 13:587-622. 1995). Unlike T cells, B cells are capable of recognizing peptides as small as 4 amino acids in length. It is the T-cell epitope/MHC complexes that are recognized by T-cell receptors leading to T cell activation.

The term "immunogenic fragment of Aβ" or "immunogenic fragment of Aβ, lacking a T-cell response," as used herein refers to an 8-mer or an Aβ fragment that is capable of inducing an immune response in the form of antibodies to Aβ, but which response does not include a T-cell response to the self antigen, Aβ.

The term "immunological" or "immune" or "immunogenic" response refers to the development of a humoral (antibody mediated) and/or a cellular (mediated by antigen-specific T cells or their secretion products) response directed against an antigen in a vertebrate individual. Such a response can be an active response induced by administration of an immunogen or a passive response induced by administration of an antibody.

The term "multivalent peptide" refers to peptides having more than one antigenic determinant.

The term "pharmaceutical composition" means a chemical or biological composition suitable for administration to a mammalian individual. As used herein, it refers to a composition comprising 8-mers, immunogenic fragments of Aβ and Aβ conjugates described herein to be administered optionally with or without an adjuvant.

DETAILED DESCRIPTION OF THE INVENTION

As previously described, preclinical studies suggest that active immunization resulting in an anti-Aβ polyclonal antibody response provides efficacy against the pathological and cognitive symptoms associated with AD in transgenic mice that overexpress the amyloid precursor protein (Bard et al., *Nature Med.*, 6: 916-919, 2000; Janus et al., *Nature*, 408: 979-982, 2000; Morgan et al., *Nature*, 408: 982-985, 2000; DeMattos et al., *Proc. Natl. Acad. Sci.*, 98: 8850-8855, 2001; Bacskai et al., *J. Neurosci.*, 22: 7873-7878, 2002; Wilcoc, et al., *J. Neurosci.*, 23: 3745-3751, 2003). These preclinical studies are supported by a single clinical trial where an aggregate form of $A\beta_{42}$ was used as an active immunogen. Preliminary evidence from this study suggests that pathological (Nicoll et al., *Nature Med.*, 9: 448-452, 2003; Ferrer et al., *Brain Pathol.*, 14: 11-20, 2004; Masliah et al., *Neurology*, 64:129-131, 2005) and cognitive improvements (Gilman et al., *Neurology*, 64 (9): 1553-1562, 2005) were found following treatment. While these findings are encouraging and consistent with preclinical studies, the treatment proved unsafe and was terminated following the appearance of meningoencephalitis in approximately 6% of the treated patients (Orgogozo et al., *Neurology*, 61: 46-54, 2003). Thus, there exists a need for active immunization procedures capable of an efficacious immune response and devoid of adverse safety issues.

Progress in understanding the nature of the adverse events in this preliminary clinical trial has been made. Several investigators have now reported the presence of CD4+ and CD8+ positive meningeal infiltrates on post-mortem evaluation (Nicoll, et al., *Nature Med.*, 9: 448-452, 2003; Ferrer et al., *Brain Pathol.*, 14: 11-20, 2004) suggestive of a T-cell response directed at the self-peptide $A\beta_{42}$. However, while those skilled in the art would recognize the need to avoid a self-directed T-cell response while maintaining an appreciable antibody response (B-cell mediated), the means to produce an agent having this property is not known. This difficulty is compounded by a lack of predictive animal models or other preclinical assays with predictive validity for these activities.

To this end, Applicants herein used the differing nature of T and B cell epitopes to design the peptides used for the invention. The vaccine constructs were designed, by restricting the linear peptide size to eight amino acids and, if necessary, removing any potential C-terminal T-cell epitope anchor residues.

Accordingly, one aspect of the present invention was the identification of Aβ fragments that are immunogenic, but lack a T-cell epitope, for use as an AD vaccine. Prior to the present application, it was not definitively known which amino acid fragments of the Aβ peptide would produce an immunogenic response that would also be deficient in a T-cell epitope. Those skilled in the art would appreciate that previous teachings in the field did not predict, for example, that an 8-mer would produce an immunogenic response and did not distinguish the usefulness of fragments from different regions of the Aβ peptide. See, for example, U.S. Pat. Nos. 6,808,712 and 6,787,144.

An additional aspect of the invention herein includes the identification of Aβ plasma elevating agents comprising an immunogenic fragment of Aβ, lacking a T-cell epitope, that induce an immune response in the form of antibodies to Aβ and that elevate plasma Aβ levels. Such agents can be used as an AD vaccine and for related amyloid diseases characterized by elevated brain Aβ levels. Prior to Applicants' invention, it was not known or predictable which immunogenic fragments of Aβ would result in elevated plasma Aβ levels. Without wishing to be bound by any theory, it is believed that the Aβ plasma elevating agents described herein act to induce an immune response in the form of antibodies to Aβ that, according to the peripheral sink theory of Aβ clearance, produce elevated levels of plasma Aβ that leads to subsequent decreases in brain Aβ. Moreover, while individual 8-mers or immunogenic fragments of Aβ may be capable of inducing an immune response such that plasma Aβ levels are elevated, Applicants found that a multivalent branched MAP, Aβ (3-10)/(21-28) (Construct No. 12, FIG. 6A), conjugated to OMPC, was particularly effective in elevating plasma Aβ levels relative to those of its constituent monomeric constructs, Aβ (3-10) (SEQ ID NO: 69) or Aβ (21-28) (SEQ ID NO: 73).

Amyloid Diseases

The invention provides compositions and methods for prophylactic and therapeutic treatment of disease characterized by accumulation of amyloid deposits. Amyloid deposits comprise a peptide aggregated to an insoluble mass. The nature of the peptide varies in different disease but in most cases, the aggregate has a β-pleated sheet structure and stains with Congo Red dye. Diseases characterized by amyloid deposits include Alzheimer's disease (AD), both late and early onset. In both diseases, the amyloid deposit comprises a peptide termed amyloid beta (Aβ), which accumulates in the brain of affected individuals. Thus, the term "amyloid disease" also refers to disease characterized by elevated brain Aβ levels.

Therapeutic Agents

Therapeutic agents for use in the present invention induce an immune response in the form of antibodies to Aβ. Induction of an immune response can be active as when an immunogen is administered to induce antibodies or T cells reactive with Aβ in an individual or passive, as when an antibody is administered that itself binds to Aβ in the individual.

The therapeutic agent to be used in preventing or treating amyloid diseases, such as AD, include peptide fragments of Aβ, which can be any of the naturally occurring forms (i.e. Aβ39, Aβ40, Aβ42, Aβ42, or Aβ43). These sequences are known in the art, see, for example, Hardy et al., TINS 20: 155-158, 1997.

As used herein, the therapeutic agent is, in a preferred embodiment, an immunogenic fragment, lacking a T-cell epitope, capable of inducing an immune response in the form of antibodies to Aβ. The immunogenic fragment of Aβ can be in the form of an 8-mer, a multivalent linear Aβ conjugate having at least one PEG spacer or a multivalent branched MAP Aβ conjugate. The therapeutic agent can be administered in the form of a pharmaceutical composition. In an another embodiment, the therapeutic agent is an Aβ plasma elevating agent capable of inducing an immune response in the form of antibodies to Aβ and that elevate plasma Aβ levels in an individual. Such agents can comprise a naturally occurring peptide fragment or may include one or more substitutions, additions or deletions, and may include synthetic or non-naturally occurring amino acids. Fragments and constructs can be screened for prophylactic and therapeutic efficacy in the assays described in the examples herein.

While in a preferred embodiment the therapeutic agents comprise a peptide fragment of Aβ, such agents may also include peptides and other compounds that do not necessarily have a significant amino acid sequence similarity with Aβ, but that nevertheless can serve as mimetics of Aβ and induce a similar immune response. For example, peptides and proteins forming β-pleated sheets can be screened for suitability for the invention herein. Similarly, combinatorial libraries and other compounds can be screened for suitability for the invention herein.

Such identified therapeutic agents can be linked either chemically or biologically to a carrier to facilitate their use as an immunogen. Such carriers include serum albumins, keyhole limpet hemocyanin (KLH), immunoglobulin molecules, ovalbumin, tetanus toxoid protein, or a toxoid from other pathogenic bacteria, such as diphtheria, *E. coli*, cholera, or *H. pylori*, or an attenuated toxin derivative. In a preferred embodiment of the invention the carrier is the outer membrane protein complex of *Neisseria meningitides* (OMPC).

The invention herein also contemplates the use of such therapeutic agents in a pharmaceutical composition comprising an 8-mer or immunogenic fragment of Aβ, which may be linked to a carrier, to be administered optionally with an adjuvant. Suitable adjuvants include aluminum salts (alum), a lipid, such as 3 De-O-acylated monophosphoryl lipid A (MPL) or a saponin-based adjuvant. In a preferred embodiment the adjuvant is an aluminum adjuvant (Merck alum adjuvant, MAA) or a saponin-based adjuvant (ISCOMATRIX®, CSL Ltd, Parkville, Australia.

Treatment Regimes

Effective doses of the compositions of the invention herein for the prophylactic or therapeutic treatment of AD and other amyloid diseases will vary depending upon many factors including, but not limited to, means of administration, target site, physiological state of the patient, other medications administered and whether treatment is a therapeutic, i.e. after on-set of disease symptoms, or prophylactic, i.e. to prevent the on-set of disease symptoms. In a preferred embodiment the patient is human and the therapeutic agent is to be administered by injection.

The amount of immunogen or therapeutic agent to be employed will also depend on whether an adjuvant is to be administered either concomitantly or sequentially, with higher doses being employed in the absence of an adjuvant.

The amount of an immunogen or therapeutic agent to be administered will vary, but amounts ranging from 0.5-50 μg of peptide (based on the Aβ peptide content) per injection are considered for human use. Those skilled in the art would know how to formulate compositions comprising antigens of the type described herein.

The administration regimen would consist of a primary immunization followed by booster injections at set intervals. The intervals between the primary immunization and the booster immunization, the intervals between the booster injections, and the number of booster immunizations will depend on the antibody titers and duration elicited by the vaccine. It will also depend on the functional efficacy of the antibody responses, namely, levels of antibody titers required to prevent AD development or exerting therapeutic effects in AD patients. A typical regimen will consist of an initial set of injections at 1, 2 and 6 months. Another regimen will consist of initial injections at 1 and 2 months. For either regimen, booster injections will be given either every six months or yearly, depending on the antibody titers and durations. An administration regimen can also be on an as-needed basis as determined by the monitoring of immune responses in the patient.

Identification of AD Vaccine Epitopes

In order to determine which 8-amino acid fragments ("8-mers") of the Aβ peptide were sufficient to produce an immunogenic response, Applicants systematically scanned the entire length of $A\beta_{42}$ with small (8 amino acids) overlapping synthetic peptides derived from the naturally occurring Aβ sequence (SEQ ID NO. 1) as shown in FIG. 1 (SEQ ID NOS: 2-37). Twenty nine overlapping eight amino acid peptides, spanning the entire length of $A\beta_{42}$, were synthesized (FIG. 2A) for use as antigens. To improve solubility, several of the peptides were modified by the addition of triple lysine (KKK) (SEQ ID NOS: 52, 53, 54, 56, 59, 60, 62, 64 and 65) or glutamine (EEE) (SEQ ID NOS: 50, 51 and 61) residues or the use of a polyethelyene glycol (PEG) (SEQ ID NOS: 55 and 63) spacer. For this reason, peptides spanning the sequences of Aβ corresponding to residues (11-18) and (13-20) were made in multiple forms, the first with a 6-aminohexanoic acid (Aha) spacer plus a functional group for chemical cross-linking at N-terminus and the other form with Aha and the functional group at C-terminus. As a control, Applicants included a longer peptide, Aβ (1-18).

As used herein, the immunogenic fragments may be 8-mer peptides (eight amino acid residues) derived from the naturally occurring, i.e. wild type, or synthetic Aβ (SEQ ID NO:1) or any mutation or variation thereof. Such mutation or variant can be produced by synthetic or recombinant means known to those of ordinary skill in the art. One example of such a variant is the EV substrate (EVEFRHDSGYEVHHQKLVF-FAEDVGSNKGAIIGLMVGGVVIA) (SEQ ID NO: 66) a peptide corresponding to Aβ (1-42) in which positions 1 and 2 of wild type Aβ have been varied.

Aβ Conjugates for Use in Vaccine Formulation

Selection of Aβ conjugates for use in formulating a vaccine was based on the immunogenicity of the 8-mers. In order to determine the immunogenicity of the 8-mer in a species with a sequence identical to the human Aβ sequence, the 29 peptides (FIG. 2A) were conjugated to KLH to form an Aβ conjugate and tested in guinea pigs (FIG. 3). As a control immunogen, Aβ (1-18)-KLH (SEQ ID NO: 37) was included in this analysis.

Guinea pigs were immunized as described in Example 3.B with conjugated immunogens formulated in alum plus 50 μg of ISCOMATRIX® (CSL, Ltd., Parkville, Australia). In order to distinguish immunogenic from non-immunogenic Aβ$_{42}$ fragments, guinea pigs were immunized three times at four week intervals. Three weeks after each immunization, blood samples were collected and tested by ELISA for antibody titers against Aβ$_{40}$ peptide. These titers are shown in FIG. 3 as post-dose 1 (PD1), post-dose 2 (PD2) and post-dose 3 (PD3), respectively.

Following the first injection (PD1) some peptide regions elicited appreciable antibody titers as did the 18-mer control. In particular, Aβ conjugates corresponding to Aβ amino acids 1-8, 2-9, 3-10, 17-24, 21-28, and 33-40 all produced titers in excess of 1:800. After the second injection (PD2), 15 of the Aβ conjugates elicited antibody titers in excess of 1:1000. Analysis at post-dose 3 (PD3) further confirmed that certain regions of Aβ are more immunogenic relative to others. Eleven regions demonstrated titers greater than 1:6000. These included regions corresponding to Aβ amino acids 1-8, 3-10, 7-14, 11-18, 13-20, 15-22, 19-26, 21-28, 23-30, 27-34 and 29-36. Of these regions, five regions were highly immunogenic (>1:10000) including: regions 1-8, 15-22, 21-28, 23-30 and 29-36. This data suggests that certain 8-amino acid regions of Aβ are highly immunogenic, while other regions (e.g., 5-12, 25-32, 31-38 and 35-42) are non-immunogenic (titers<1:300). The results also demonstrate that while the Aβ conjugates were capable of eliciting an Aβ$_{40}$ peptide-specific antibody response, not all fragments of Aβ were equally immunogenic.

Immunoreactivity of Aβ Peptide-KLH Conjugates

In order to demonstrate that the immune sera generated from the guinea pigs following immunization with the Aβ peptide-KLH conjugates is relevant to human AD, a study was performed to evaluate the immunoreactivity of polyclonal sera from a guinea pig immunized with an Aβ (3-10)-KLH (SEQ ID NO: 40) conjugate. The serum sample collected four weeks following the second injection of Aβ (3-10)-KLH (SEQ ID NO: 40) conjugate from a guinea pig was tested for reactivity with human AD brain tissues by immunohistochemistry (Example 4).

As depicted in FIG. 4 the immunogenic response produced by the Aβ (3-10)-KLH (SEQ ID NO: 40) conjugate produced an antibody response that was directed against human AD brain tissue. FIG. 4A demonstrates immunoreactivity of the monoclonal anti-Aβ antibody 6F3D (Vector Laboratories). As shown, this brain has extensive Aβ deposits in a manner expected to be typical for human AD. FIG. 4B demonstrates a lack of immunoreactivity of sera from a pre-immunized guinea pig. FIG. 4C shows positive immunoreactivity of sera from this same guinea pig following two injections of the Aβ (3-10)-KLH (SEQ ID NO: 40) conjugate. Collectively, this data demonstrates that the immunogenicity found by ELISA contains a significant antibody response directed against human Aβ found in this AD tissue. These results confirm and extend the unexpected finding of the differential immunogenicity imparted by particular fragments of Aβ to further demonstrate that this response is directed in a manner consistent with a therapeutic application.

Generation of OMPC Conjugates and Multiple Antigenic Conjugates

On the basis of immunogenicity in guinea pigs, the relative location of the peptide fragment within the Aβ$_{42}$ amino acid sequence, the solubility of the Aβ fragments and the feasibility of using OMPC as a carrier protein, Applicants selected seven 8-mers (FIG. 2B) for OMPC conjugation. These peptide fragments correspond to the following amino acid regions of Aβ: 1-8, 2-9, 3-10, 7-14, 17-24, 21-28 and 33-40.

The invention described herein includes multivalent peptide conjugates such as those shown in FIGS. 5, 6A and 6B. Multivalent branched MAP-OMPC conjugates (FIGS. 6A and 6B) were generated by using a lysine-based scaffold, whereas multivalent linear 8-mer-OMPC conjugates (FIG. 5) were prepared using a PEG linker. Those skilled in the art will appreciate that a PEG linker, compared to conventional amino acid linkers that can also be used herein, offers the advantage of lower immunogenicity and greater peptide solubility. In a preferred embodiment of the invention, the immunogenic fragment is a multivalent MAP conjugated to OMPC. It should be understood by those skilled in the art that such a conjugation is not a 1:1 ratio of peptide to carrier. Rather, a plurality of peptides is attached in a spherical manner to each OMPC molecule. It will be further appreciated by those skilled in the art that the use of multivalent linear constructs and MAPs will enhance solubility, formulation stability, immunogenicity and the diversity of the polyclonal response.

Immunogenicity of OMPC Conjugate Vaccines

In an effort to evaluate the immunogenicity of an Aβ peptide-OMPC conjugate and to further evaluate the benefit of an adjuvant with this vaccine construct, Applicants initiated a study in rhesus monkeys. Rhesus monkeys were vaccinated with an Aβ (1-18)-OMPC conjugate (dose based on the Aβ peptide content), which was formulated either in Merck alum adjuvant (MAA) or MAA and ISCOMATRIX® (CSL, Ltd., Parkville, Australia). Blood samples were collected and used to determine the antibody titers against Aβ$_{40}$. Interim analysis of this ongoing study demonstrated that at post-dose 1 (PD1) the monkeys receiving 5 µg vaccine in alum failed to develop any detectable titers, while those receiving 30 µg vaccine in alum developed low Aβ$_{40}$ specific titers. All monkeys that received the alum plus ISCOMATRIX® formulation developed significant antibody titers. At post-dose 2 (PD2) both doses of the Aβ conjugate in alum alone produced similar titer levels, whereas the cohorts receiving the alum plus ISCOMATRIX® developed 10-fold higher antibody titers relative to the alum alone cohorts. The results of this study confirmed that the Aβ-OMPC conjugate is immunogenic in non-human primates. The data further demonstrated that the efficacy of such a conjugate vaccine is significantly enhanced by a saponin-based adjuvant such as ISCOMATRIX®.

EXAMPLES

Example 1

Preparation of Aβ Conjugates

This example describes the preparation of Aβ peptide fragments subsequently used for the Aβ conjugates to induce an immune response in the form of antibodies to Aβ.

A. Preparation of Aβ3 (8-mers) Peptides (SEQ ID NOS.: 37-65; FIG. 2A)

The peptides intended for conjugation to maleimide derivatized carrier proteins were synthesized with a cysteine residue at the carboxy terminus. The spacer, Aha (6-aminohexanoic acid) was incorporated between the primary peptide sequence and the carboxy terminal cysteine as a structural element for minimizing steric accessibility to carrier protein during conjugation. Additionally, solubilizing residues represented by EEE, KKK or PEG were introduced at the C-terminus in sequences 14, 15, 16 17, 18, 19, 20, 23, 24, 25, 26, 27, 28, 29. The PEG unit was introduced as, O—(N-Fmoc-2-aminoethyl)-O'-(2-carboxyethyl)-undecaethyleneglycol [Fmoc-NHCH$_2$CH$_2$O(CH$_2$CH$_2$O)$_{10}$CH$_2$CH$_2$OCH$_2$CH$_2$CO$_2$H].

Starting with Rink Amide MBHA resin the Aβ peptides were prepared by solid-phase synthesis on an automated peptide synthesizer using Fmoc chemistry protocols as supplied by the manufacturer (Applied Biosystems, Foster City, Calif.). Following assembly the resin bound peptide was deprotected and cleaved from the resin using a cocktail of 94.5% trifluoroacetic acid, 2.5% 1,2-ethanedithiol, 1% triisopropylsilane and 2.5% $H_2O$. Following a two hour treatment the reaction was filtered, concentrated and the resulting oil triturated with ethyl ether. The solid product was filtered, dissolved in 50% acetic acid/$H_2O$ and freeze-dried. Purification of the semi-pure product was achieved by RPHPLC using a 0.1% TFA/$H_2O$/acetonitrile gradient on a C-18 support. Fractions were evaluated by analytical HPLC. Pure fractions (>98%) were pooled and freeze-dried. Identity was confirmed by amino acid analysis and mass spectral analysis.

B. Preparation of Aβ peptide-KLH Conjugates (SEQ ID NOS.: 37-65; FIG. 2A)

For preparing the KLH conjugates, the Aβ peptides (8-mers), 2 mg, containing a C-terminal cysteine was suspended in 1 ml of commercial maleimide conjugation buffer (83 mM sodium phosphate, 0.1 M EDTA, 0.9 M NaCl, 0.02% sodium azide, pH 7.2 (Pierce Biotechnology, Rockford, Ill.). A 2 mg sample of commercial maleimide-activated KLH (Pierce Biotechnology, Rockford, Ill.) was added to the peptide and allowed to react at 25° C. for four hours. The conjugate was separated from unreacted peptide and reagents by exhaustive dialysis versus PBS buffer using 100,000 Da dialysis tubing. The amount of peptide incorporated into the conjugate was estimated by amino acid analysis following a 70 hour acid hydrolysis. Peptide concentrations were determined to be between 0.24 and 0.03 mg/ml.

C. Synthesis of Bromoacetylated Aβ Peptides (SEQ ID NOS.: 67-77; FIG. 2B)

Bromoacetylated peptides were prepared by standard t-Boc solid-phase synthesis, using a double coupling protocol for the introduction of amino acids on the Applied Biosystems model 430A automated synthesizer. Starting with p-methylbenzhydrylamine resin the carboxy terminal amino acid t-Boc-Lys (Fmoc)-OH was introduced followed by the subsequent amino acids in the sequence. Aha was introduced as a spacer to all of these sequences and a PEG unit in sequences 35 and 37 to aid in aqueous solubility. The PEG unit was introduced as O—(N-Boc-2-aminoethyl)-O'—(N-diglycolyl-2-aminoethyl) hexaethyleneglycol [Boc-NHCH$_2$CH$_2$O(CH$_2$CH$_2$O)$_6$CH$_2$CH$_2$NHCOCH$_2$OCH$_2$CO$_2$H]. The amino terminus was capped by the coupling of acetic acid. After assembly of the primary sequence the Fmoc protecting group on the epsilon amino group of the carboxy terminal lysine was removed by treatment with piperidine. Subsequently the N$^\epsilon$ amino group was reacted with Bromoacetic anhydride in methylene chloride as the solvent for 30 minutes. Deprotection and removal of the peptide from the resin support were achieved by treatment with liquid hydrofluoric acid and 10% anisole as a scavenger. The peptides were purified by preparative HPLC on reverse phase C-18 silica columns using a 0.1% TFA/acetonitrile gradient. Identity and homogeneity of the peptides were confirmed by analytical HPLC and mass spectral analysis.

D. Synthesis of Bromoacetylated Divalent MAP, Construct No. 8, FIG. 6A

The synthesis of bromoacetylated branched multiple antigenic peptides (MAPs) is similar to that described in Example 1.C. Following coupling of the carboxyterminal Fmoc-Lys (ivDde)-OH [ivDde=1, (4,4-Dimethyl-2,6-dioxo-cyclohexylidene)-3-methyl-butyl] to MBHA resin the α-amino Fmoc protecting group was removed using piperidine and the synthesis continued with the introduction of t-Boc-Lys(Fmoc)-OH. After deprotection of the t-Boc group the sequence was extended with the following t-Boc protected amino acids: Aha, Y, G, S, D, H, R, F, E and the amino terminus capped by coupling acetic acid on the ABI synthesizer. The side chain lysine Fmoc protecting group was removed with piperidine and the N$^\epsilon$ arm of lysine extended on the ABI synthesizer with the introduction of the following protected amino acids: Aha, H, H, V, E, Y, G, S, D and the amino terminus capped by coupling acetic acid. Removal of the ivDde protecting group was by treatment with 5% hydrazine in dimethylformamide for 5 minutes providing the unblocked N$^\epsilon$ amino group on the carboxy terminal lysine which was further elaborated with bromoacetic anhydride as described in Example 1.C. Cleavage of the peptide from the resin, its subsequent purification and characterization are as described in Example 1.C.

E. Synthesis of Bromoacetylated MAPs, Construct Nos. 11 and 12, FIG. 6A

MAP Constructs Nos. 11 and 12 were prepared as described in Example 1.D.

F. Synthesis of Cysteine Multivalent MAP, Construct No. 9, FIG. 6A

Starting with MBHA resin the following t-Boc protected amino acids were assembled on the ABI automated synthesizer C, Lys(Fmoc), Aha, Y, G, S, D, H, R, F, E followed by coupling with acetic acid. The N$^\epsilon$ amino Fmoc protecting group of lysine was removed and the synthesis continued with the introduction of the following t-Boc protected amino acids: Aha, H, H, V, E, Y, G, S, D followed by coupling with acetic acid. The resin bound peptide was isolated, purified and characterized as in Example 1.C. Note: Instead of 10% anisole as in Example 1.C, a 1:1 mixture of p-cresol: p-thiocresol was used as a scavenger during HF cleavage.

G. Synthesis of Cysteine Divalent MAPs, Construct Nos. 10, 13 and 14, FIG. 6A

Divalent MAPs, Construct Nos. 10, 13 and 14, FIG. 6A, were prepared as described in Example 6.F. The PEG unit was introduced as O—(N-Boc-2-aminoethyl)-O'—(N-diglycolyl-2-aminoethyl) hexaethyleneglycol (t-Boc-NHCH$_2$CH$_2$O(CH$_2$CH$_2$O)$_6$CH$_2$CH$_2$NHCOCH$_2$OCH$_2$CO$_2$H).

H. Synthesis of Bromoacetylated Multivalent MAP, Construct No. 16, FIG. 6B

Using the ABI automated synthesizer Fmoc-Lys (t-Boc)-OH was coupled to MBHA resin. Following removal of the t-Boc protecting group on the N$^\epsilon$ amino group of lysine the sequence was extended with the introduction of the following t-Boc protected amino acids: Aha, Y, G, S, D, H, R, F, E, followed by coupling of acetic acid. The Nα Fmoc protecting group on lysine was removed by manual treatment with piperidine. The sequence was further elaborated (on ABI synthesizer) with the introduction of Fmoc-Lys (t-Boc)-OH followed by the following t-Boc protected amino acids: Aha, H, H, V, E, Y, G, S, D and coupling of acetic acid. The lysine Fmoc N$^\alpha$ amino protecting group was removed as previously described and the synthesis continued with the introduction of Fmoc-Lys(t-Boc)-OH followed by the t-Boc protected amino acids: Aha, K, N, S, G, V, D, E, A and acetic acid coupling. The N$^\alpha$ Fmoc protecting on lysine was removed and the synthesis continued with the introduction Fmoc-Lys (t-Boc)-OH followed by the following t-Boc protected amino acids: Aha, V, V, G, G, V, M, L, G and acetic acid coupling. Following removal of the Nα Fmoc protecting group of lysine the resin bound peptide was reacted with bromoacetic anhydride as in Example 1.C. Isolation and characterization of the final product was as in Example 1.C.

I. Synthesis of Multivalent MAPs, Construct Nos. 15 and 17, FIG. 6B

The synthesis of MAP Aβ, conjugates, Construct Nos. 15 and 17, FIG. 6B, are as described in Example 1.F and 1.H.

J. Synthesis of Bromoacetylated Multivalent Linear Peptide, Construct No. 1, FIG. 5

Starting with MBHA resin the primary sequence was synthesized using t-Boc chemistry on the ABI automated synthesizer as described in Example 6.A. The interspaced PEG units were manually introduced as the Fmoc-1-amino-4,7,10-trioxa 13-tridecanamine succinic acid [Fmoc-NHCH$_2$CH$_2$CH$_2$O(CH$_2$CH$_2$O)$_2$CH$_2$CH$_2$CH$_2$NHCOCH$_2$CH$_2$CO$_2$H] using BOP reagent as the coupling agent. Piperidine was used for deprotection of the Fmoc group. Bromoacetylation of the amino terminus was as described in Example 1.C. Isolation and characterization of the desired product was as in Example 1.C.

K. Synthesis of Multivalent Linear Aβ Peptides, Construct Nos. 2, 5, 6 and 7, FIG. 5

The synthesis of multivalent linear Aβ peptides, Construct Nos. 2, 5, 6 and 7 are as described in Example 1.J.

Example 2

Chemical Conjugation of Aβ Peptides to OMPC

This example presents the chemical conjugation of peptides derived from human Aβ$_{42}$ to purified Outer Membrane Protein Complex (OMPC) of *Neisseria meningitidis*, type B. The chemical nature of the coupling is reaction between haloacetyl-derivatized peptide and thiol-derivatized protein of the membrane complex. Amyloid peptides were synthesized as described above with a bromoacetyl functionality on the N-terminus for divalent linear epitope peptides or on the C-terminus or attached through the epsilon amino group of a lysine residue for monovalent linear and branched MAP forms. The BrAc group was separated from the mature peptide by a spacer consisting of 6-aminohexanoic acid (Aha). Refer to sequences described above. Conjugation will be described for the representative peptide, Aβ (3-10). All manipulation of OMPC-containing solutions was performed in a laminar flow environment following standard aseptic techniques.

A. Thiolation of OMPC

Purified, sterile OMPC, obtainable from a process such as that described in Fu, U.S. Pat. No. 5,494,808 used for the production of PedvaxHIB® and pneumococcal conjugate vaccines, was thiolated on a portion of its surface-accessible lysine residues using the reagent N-acetylhomocysteinethiolactone (NAHT, Aldrich, St. Louis, Mo.). OMPC in water, 117 mg, was pelleted by centrifugation at 289,000×g for 60 minutes at 4° C. and the supernatant was discarded. N2-sparged activation buffer (0.11 M sodium borate, pH 11) was added to the centrifuge tube and the pellet was dislodged with a glass stir rod. The suspension was transferred to a glass Dounce homogenizer and resuspended with 30 strokes. The centrifuge tube was washed and the wash dounced with 30 strokes. Re-suspended pellet and wash were combined in a clean vessel to give a OMPC concentration of 10 mg/mL. Solid DTT and EDTA were dissolved in N2-sparged activation buffer and charged to the reaction vessel at a ratio of 0.106 mg DTT/mg OMPC and 0.57 mg EDTA/mg OMPC. After gentle mixing, NAHT was dissolved in N2-sparged water and charged to the reaction at the ratio of 0.89 mg NAHT/mg OMPC. Reaction proceeded for three hours at ambient temperature, protected from light in a N2 hood. At completion, OMPC was pelleted as described above and re-suspended at 6 mg/mL by Dounce homogenization in N2-sparged conjugation buffer (25 mM sodium borate, pH 8.5, 0.15 M NaCl) to wash the pellet. For final re-suspension, the OMPC was pelleted as above and re-suspended at 10 mg/mL by Dounce homogenization in N2-sparged conjugation buffer. An aliquot was removed for free thiol determination by Ellman assay and the bulk product was stored on ice in dark until use. Measured thiol content was between 0.2 to 0.3 μmol/mL.

B. Conjugation of Aβ Peptide to OMPC

Functional BrAc content of peptide was assumed to be 1:1 on a molar basis. Sufficient peptide was weighed to give a 1.6 molar excess of BrAc over total thiol. The targeted total OMPC protein for each conjugation was 15 mg. Peptides were re-suspended in N2-sparged conjugation buffer at 2.6 mg/mL and slowly added to thiolated OMPC solution. The reactions were protected from light and incubated at ambient temperature for about 22 hours. Residual free OMPC thiol groups were quenched with a 5-fold molar excess of N-ethylmaleimide for 18 hours at ambient temperature. A thiolated OMPC-only control was carried through the conjugation protocol in parallel. Upon completion of quenching, conjugate and control were transferred to 100,000 Da molecular weight cut-off dialysis units and dialyzed exhaustively against at least five changes of conjugation buffer. Upon completion of dialysis, samples were transferred to 15 ml polypropylene centrifuge tubes and centrifuged at 2,280×g for five minutes at 4° C. to remove any aggregated material. Aliquots were removed for analysis and the bulk was stored at 4° C.

C. Analysis of Aβ Peptide-OMPC Conjugates

Total protein was determined by the modified Lowry assay and samples of conjugate and control were analyzed by quantitative amino acid analysis (AAA). Peptide to OMPC molar ratios were determined from quantitation of the unique residue S-carboxymethylhomocysteine which was released upon acid hydrolysis of the nascent peptide-OMPC bond. The OMPC-specific concentration was determined from hydrolysis-stable residues which were absent from the peptide sequence and thus unique to OMPC protein. Assuming 1 mol of peptide for every mol SCMHC, the ratio of SCMHC/OMPC was thus equivalent to the peptide/OMPC content. The mass loading of peptide could be calculated from this ratio using the peptide molecular weight and an average OMPC mass of 40,000,000 Da.

The covalent nature of the conjugation was qualitatively confirmed by SDS-PAGE analysis using 4-20% Tris-glycine gels (Invitrogen, Carlsbad, Calif.) where an upward shift in mobility was observed for the Coomassie-stained conjugate bands relative to control.

The calculated molar loading ratios (mol peptide/mol OMPC) for all conjugated BrAc peptides were:

| Peptide | Peptide Mw | Peptide/OMPC (mol/mol) |
|---|---|---|
| Aβ (3-10) - BrAc | 1,412 | 2,793 |
| Ab (7-14) - BrAc | 1,344 | 2,283 |
| Ab (21-28) - BrAc | 1,222 | 2,126 |
| Ab (17-24) - BrAc | 1,809 | 1,795 |
| Ab (33-40) - BrAc | 1,601 | 2,139 |
| A-D-MAP-BrAc | 2,498 | 2,173 |

-continued

| Peptide | Peptide Mw | Peptide/OMPC (mol/mol) |
|---|---|---|
| A-B-MAP-BrAc | 2,622 | 2,147 |
| BrAc-linear-D-A | 2,649 | 2,263 |
| BrAc-linear-B-A | 2,773 | 2,178 |
| Aβ (1-8) - BrAc | 1,378 | 2,759 |
| F-D-MAP-BrAc | 2,463 | 1,318 |
| BrAc-linear-D-F | 2,615 | 1,812 |
| F-G-A-D-MAP-BrAc | 5,111 | 636 |

Example 3

Immunogenicity of Aβ Conjugates

This example describes the formulation and administration of the Aβ conjugates capable of inducing an immune response in the form of antibodies to Aβ.

A. Formulation of Vaccine Conjugates

The Aβ peptide-KLH conjugate vaccines were formulated in ISCOMATRIX® (CSL Ltd., Parkville, Australia). All Aβ peptide-OMPC conjugate vaccines were formulated in alum, either with or without a second adjuvant, such as the saponin-based adjuvant, ISCOMATRIX® (CSL Ltd., Parkville, Australia). All the sample manipulations were performed under sterile conditions.

For the alum formulations, conjugates are diluted one times saline at a designated peptide concentration and mixed with two times alum (Merck, Product No. 39943), which corresponds to 900 µg/mL Merck alum prepared in sterile saline (150 mM sterile sodium chloride solution). Thus, target concentration in the vaccine is 450 µg/mL Merck alum or one time Merck alum. Target peptide (antigen) concentrations for animal studies were as follows: for mice—12.1 µg/mL (Dose 0.1 mL); for monkeys—10 µg/mL or 60 µg/mL (Dose 0.5 mL) and for guinea pigs—12.5 µg/mL (Dose 0.4 mL). The mix is incubated for two hours at room temperature. To obtain the injection dose, the alum-absorbed conjugates are diluted with one time alum to reach the target peptide concentration. Where a second adjuvant is needed, i.e. ISCOMATRIX®, the target concentration was 10 µg/ML for mice studies, 0, 100 or 200 µg/mL for monkey studies and 125 µg/mL for guinea pigs.

1. ISCOMATRIX® Preparation

Using a cassette membrane (Slide-A-Lyzer® Dialysis Cassett, 10K MWCO, Pierce, Rockford, Ill.), ISCOMATRIX® is dialyzed into sterile saline solution at 2-8° C. Sterile saline solution is changed 2-3 times during dialysis. After completion of dialysis, ISCOMATRIX® is filter sterilized using a syringe filter (0.22 µM Millex-GV syringe filter, Millipore, Billerica, Mass.). The concentration of sterile, dialyzed ISCOMATRIX® is determined by RP-HPLC. ISCOMATRIX® is stored sterile at 2-8° C. until use.

2. Aβ Peptide-OMPC Conjugate and Merck Alum Preparation

Aβ peptide-OMPC conjugate stocks are diluted into sterile 1× saline solution. The diluted AD peptide-OMPC conjugate stocks are then added to 2× Merck alum in 1× sterile saline solution and mixed for one hour on a rotating wheel at room temperature. The mixture is allowed to settle on the bench top for 15 minutes at room temperature and is then centrifuged at 1500 rpm for ten minutes. The supernatant is decanted off gently (UV analysis of supernatant is performed to determine % Aβ peptide-OMPC conjugate bound to alum) and the pellet is resuspended in sterile 1× saline. The mixture is aliquoted into sterile 3 mL tubing glass vials and then stored at 2-8° C. until final formulation with ISCOMATRIX®

3. Formulation of Aβ Peptide-OMPC/Alum and ISCOMATRIX® Vaccine

Prior to final formulation with ISCOMATRIX®, the particle size of the Aβ peptide-OMPC/alum in saline is determined by static light scattering to confirm binding and monitor particle stability. The sterile, dialyzed ISCOMATRIX® in 1× saline is added to Aβ peptide-OMPC/alum in sterile 150 mM NaCl while vortexing. Vials are stoppered, capped and crimped to completely seal. Vaccine is stored at 2-8° C. prior to injection. Prior to injection, each vaccine is vortexed for 3-5 minutes.

B. Immunogenicity of Conjugate Vaccines in Guinea Pigs

Six to ten week old female guinea pigs were obtained from Harlan Inc., Indianapolis, Iowa and maintained in the animal facilities of Merck research Laboratories in accordance with institutional guidelines. All animal experiments were approved by Merck Research Laboratories Institutional Animal Care and Use Committee (IACUC). Antigens were prepared in phosphate-buffered saline and formulated in the designated adjuvant.

Two animals per group were immunized with the Aβ peptide—KLH conjugates shown in FIG. 2A intramuscularly with 400 µl of a conjugate vaccine (8 µg by peptide content or 50 µg by total conjugate) in the presence of 40 µg of ISCOMATRIX®. The immunizations were performed three times in four-week intervals. Serum samples were collected before first immunization (pre-bleeds) and three weeks after each immunization and stored at 4° C. prior to antibody titer determinations. The antibody titers were determined by ELISA according to the protocol that follows using $A\beta_{40}$ as the target antigen.

The ELISA based analysis is as follows: Ninety six-well plates were coated with 50 µl per well of Aβ at a concentration of 4 µg/ml in 50 mM bicarbonate buffer, pH 9.6, at 4° C. overnight. Plates were washed with phosphate buffered saline (PBS) and blocked with 3% skim milk in PBS containing 0.05% Tween-20 (milk-PBST). Testing samples were diluted in a 4-fold series in PBST. One hundred µl of a diluted sample was added to each well, and the plates were incubated at 24° C. for two hours and then washed six times with PBST. Fifty µl of HRP-conjugated secondary antibodies at 1:5000 dilution in milk-PBST was added per well and the plates were incubated at 24° C. for one hour. The plates were washed three times and 100 µl of 1 mg/ml o-phenylenediamine dihydrochloride in 100 mM sodium citrate, pH 4.5 was added per well. After 30 minutes incubation at 24° C., the reaction was stopped by adding 100 µl of 1 N $H_2SO_4$ per well, and the plates were read at 490 nm using an ELISA plate reader. The antibody titer was defined as the reciprocal of the highest dilution that gave an OD490 nm value above the mean plus two standard deviations of the conjugate control wells.

The results of this analysis, shown in FIG. 3, demonstrated that following the first injection (PD1) some peptide regions elicited appreciable antibody titers as did the 18-mer control. In particular, Aβ peptide fragments corresponding to Aβ amino acids 1-8, 2-9, 3-10, 17-24, 21-28, and 33-40 all produced titers in excess of 1:800. After the second injection (PD2), 15 of the 8-mer conjugates elicited antibody titers in excess of 1:1000. Analysis at post-dose 3 (PD3) further confirmed that certain regions of the Aβ peptide were more immunogenic relative to others. Eleven regions demonstrated titers greater than 1:6000. These included regions corresponding to Aβ amino acids 1-8, 3-10, 7-14, 11-18, 13-20, 15-22, 19-26, 21-28, 23-30, 27-34 and 29-36. Of these regions, five regions were highly immunogenic (>1:10000) including: regions 1-8, 15-22, 21-28, 23-30 and 29-36. The results demonstrate that 8-mer conjugates are capable of eliciting an $A\beta_{40}$ specific antibody response. Unexpectedly, and contrary to previous teachings, not all fragments of $A\beta$ were equally immunogenic. In fact, these data suggest that certain 8-mers are highly immunogenic, while other regions of $A\beta$ (e.g., 5-12, 25-32, 31-38 and 35-42) are non-immunogenic (titers<1:300).

C. Immunogenicity of Conjugate Vaccines in Rhesus Monkeys

A study was conducted in non-human primates, i.e. rhesus monkeys, comparable to that done with guinea pigs to determine whether $A\beta$ peptide-OMPC conjugates and an alum and ISCOMATRIX® adjuvant provided an immune response. Rhesus monkeys (*Macaca mulatta*) were maintained in accordance with the institutional animal care protocols of Merck Research Laboratories and New Iberia Research Center (The University of Louisiana at Lafayette, New Iberia, La.).

Applicants used $A\beta$ peptides conjugated to OMPC as the model antigens, including, the 8-mers shown in FIG. 2B: $A\beta$ (1-8) (SEQ. ID NO: 67), $A\beta$ (3-10) (SEQ. ID NO: 69), $A\beta$ (7-14) (SEQ ID NO: 70), $A\beta$ (17-24) (SEQ ID NO. 72), $A\beta$ (21-28) (SEQ ID NO: 73) and $A\beta$ (33-40) (SEQ ID NO. 74); the divalent linear peptides shown in FIG. 5: $A\beta$ (3-10) (7-14) (Construct No. 1), $A\beta$ (3-10) (21-28) (Construct No. 2), $A\beta$ (1-8)(21-28) (Construct No. 5); and the multivalent branched MAPs shown in FIG. 6A: $A\beta$ (3-10)(7-14) (Construct No. 8), $A\beta$ (1-8)(21-28) (Construct No. 11), $A\beta$ (3-10) (21-28) (Construct No. 12).

Rhesus macaques (N=3) were immunized with 5 µg of each of the vaccine formulated in Merck alum adjuvant (MAA) plus 100 ug of ISCOMATRIX® every four weeks. Serum samples were collected four weeks following each injection and determined for $A\beta$ specific antibody responses by ELISA. Consistent with the results from the guinea pig studies, all conjugates were found to be immunogenic in monkeys. $A\beta$ specific antibody titers were detectable after single injections and further boosted after the subsequent injections. Generally for the conjugates tested, the peak titers were reached after the second or third immunization where geometric mean titers ranged from 25,000 to 500,000. These results confirm the finding that the $A\beta$ conjugates described herein are capable of eliciting an $A\beta$ specific antibody response.

D. Adjuvant Effect on Immunogenicity of Conjugate Vaccines in Rhesus Monkeys

An additional study was conducted in non-human primates, i.e. rhesus monkeys, to determine whether an $A\beta$ peptide-OMPC conjugate and a saponin-based adjuvant, such as ISCOMATRIX®, can provide an improved immune response. Applicants used an $A\beta$ (1-18) peptide conjugated to OMPC as the model antigen. Rhesus monkeys (*Macaca mulatta*) were maintained in accordance with the institutional animal care protocols of Merck Research Laboratories and New Iberia Research Center (The University of Louisiana at Lafayette, New Iberia, La.).

Five groups of monkeys, three per group, were given the following $A\beta$ (1-18)-OMPC conjugates: (1) 5 µg conjugate (based on peptide content) in alum, (2) 5 µg conjugate in alum+100 µg ISCOMATRIX®, (3) 5 µg conjugate in alum+50 mg ISCOMATRIX®, (4), 30 µg conjugate in alum, (2) 30 µg conjugate in alum+100 µg ISCOMATRIX®. The immunizations were carried out by intramuscular injections in 0.5 ml aliquots at weeks 0, 8 and 24 using tuberculin syringes (Becton-Dickinson, Franklin Lakes, N.J.). Serum samples were collected at four week intervals starting from week 0 (pre-bleed) and the tested for antibody titers against $A\beta_{40}$ by ELISA, performed as described in the preceding example.

Interium analysis of this ongoing study demonstrated that at PD1 the monkeys receiving 5 mcg conjugate vaccine in alum failed to develop any detectable titers, while those receiving 30 µg conjugate vaccine in alum developed low $A\beta_{40}$ specific titers. All monkeys that received the alum plus ISCOMATRIX® formulation developed significant antibody titers. At PD2, both doses of immunogen in alum alone produced similar titer levels, whereas the cohorts receiving the alum plus ISCOMATRIX® developed 10-fold higher antibody titers relative to the alum alone condition. The results of this study confirmed that this $A\beta$ peptide-OMPC conjugate is immunogenic in non-human primates. The data further demonstrate that the efficacy of such a conjugate vaccine is significantly enhanced by a saponin-based adjuvant such as ISCOMATRIX®.

Example 4

Immunoreactivity of Guinea Pig Polyclonal Sera

In order to demonstrate that the immune sera generated from the guinea pigs above (Example 3.B) following immunization with 8-mer KLH conjugates is relevant to human AD, a study was performed to evaluate the immunoreactivity of polyclonal sera from a guinea pig immunized with an $A\beta$ (3-10)-KLH immunogen. Four weeks following a second injection of this construct blood was collected from a representative guinea pig according to the following methodology.

Reactivity of the polyclonal sera was evaluated on human AD brain sections (BioChain Institute, Inc., Hayward, Calif.). Human brain sections were prepared by incubating at 60° C. for thirty minutes followed by two five minute xylene washes at room temperature. Sections were subsequently immersed in 100% EtOH twice for five minute each followed by a five minute immersion in $ddH_2O$, Sections were immersed for three minutes in 99% formic acid followed by a brief wash in $ddH_2O$ and a five minute immersion in phosphate buffered solution (PBS). Sections were then incubated with a peroxidase blocker for ten minutes followed by a five minute PBS wash. Sections were blocked by a ten minute exposure to 10% goat serum followed by a five minute wash with PBS. Sections were then incubated with diluted guinea pig sera at 4° C. overnight or for one hour at room temperature. Following a five minute PBS wash, sections were incubated for ten minutes with diluted biotinylated goat anti-guinea pig IgG or biotinylated horse anti-mouse antibody (1 drop in 5 ml PBS). Sections were washed for five minutes in PBS and subsequently incubated with ABC solution (Vectorstain ABC kit; Vector Laboratories, Inc.) for thirty minutes. Sections were washed with PBS for five minutes. Sections were then stained with DAB (DakoCytomation) for five minutes and washed with dd $H_2O$. Sections were then counterstained in hematoxylin for thirty seconds and dehydrated in graded EtOH and Xylenes (70% EtOH for five minutes, 80% EtOH for five minutes, 100% EtOH for five minutes and xylenes for five minutes). Sections were then cover-slipped and evaluated by light microscopy.

The immunogenic response produced by the $A\beta$ (3-10)-KLH conjugate produced an antibody response that was directed against human AD brain tissue. As shown in FIG. 4, this human brain section has extensive $A\beta$ deposition in a manner typical to that expected for human AD. While pre-immunized guinea pig sera demonstrates a lack of immunoreactivity when exposed to this tissue, positive immunoreactivity of sera from this same guinea pig is noted following two injections of the Aβ (3-10)=–KLH construct. These data demonstrate that the immunogenicity found by ELISA, and illustrated in FIG. 3, contains a significant antibody response directed against human Aβ found in this AD tissue. Thus, the results extend the unexpected finding of differential immunogenicity by some Aβ fragments to further demonstrate that this response is directed in a manner consistent with therapeutic application.

Example 5

Identification of Immunogenic Fragments Lacking T-Cell Epitopes

To identify immunogenic fragments lacking a T-cell epitope for use in the invention herein, the following Enzyme-Linked Immunospot (ELISpot) assay can be used as a method to assess T-cell responses to a particular antigen. Immunogen fragments possessing T-cell epitopes are identified by the presence of a dark spot on the surface of a white membrane; each spot indicates the presence of a T-cell that has secreted interferon gamma (IFN-γ) in response to the antigen (i.e. immunogenic fragment). Those skilled in the art of vaccines and immunology are familiar with this assay, see, for example, Larsson et al., *AIDS* 3: 767-777, 1999, and Mwau et al., *AIDS Research and Human Retroviruses* 18: 611-618, 2002. A recent review can be found in A. E. Kalyuzhny, *Methods Mol. Biol.* 302:15-31, 2005.

Applicants used peripheral blood monocytes (PBMCs) from rhesus macaques (New Iberia Research Center, The University of Louisiana at Lafayette, New Iberia, La.) for response to the peptides Aβ1-40 (American Peptide Co., Sunnyvale, Calif.) (amino acid sequence DAEFRHDS-GYEVHHQKLVFFAEDVG SNKGAIIGLMVGGVV) (SEQ ID NO: 78) and Aβ1-20 (Synpep, Dublin, Calif.) (amino acid sequence DAEFRIDSG YEVHHQKLVFF) (SEQ ID NO: 79).

Purified monoclonal mouse anti-monkey IFN-γ (clone MD-1, Cat No. CT 525, U-CyTech biosciences, Utrecht, The Netherlands) was diluted in phosphate buffered saline (PBS) with 1% penicillin and streptomycin sulfate (GIBCO® Penicillin-Streptomycin, Cat. No. 15140-122, Invitrogen, Carlsbad, Calif.), then added to 96-well HTS IP sterile plates (Cat. No. MSIPS4W10, Millipore, Billerica, Mass.), and incubated for greater than twelve hours at 4° C. Plates were washed and R10 [RPMI medium 1640 (GIBCO® Cat. No. 11875-093), 10% Fetal bovine serum (HyClone SH30070.03, Logan, Utah), 0.1% 50 mM 2-Mercaptoethanol (GIBCO® Cat. No. 21985-023), 1% 1M HEPES Buffer (GIBCO® 15630-080), 1% 200 mM L-glutamine (GIBCO® Cat. No. 25030-081), 1% 100 mM MEM sodium pyruvate solution (GIBCO® Cat. No. 11360-070), 1% penicillin-streptomycin solution (GIBCO® Cat. No. 15140-122)] was added before incubation for at least two hours at 37° C. PBMCs were centrifuged and re-suspended in R10. PBMCs were counted on a Z2 Coulter counter (Beckman Coulter, Fullerton, Calif.). Each well of the aspirated plate received either 0.4 µg of Aβ 1-40, Aβ 1-20, PHA (phytohemagglutinin, Cat No. L-8902, Sigma, St. Louis, Mo., positive control), or diluted DMSO (Sigma, negative control); 400000 PBMCs were then added to each well. Plates were incubated for 18-24 hours at 37° C. in a humid $CO_2$ incubator. Plates were washed in PBS with 5% FBS and 0.005% Tween; biotin-conjugated anti-monkey IFN-γ polyclonal antibodies (U-CyTech biosciences, Utrecht, The Netherlands) were diluted in the same media and added to each plate; plates were then incubated at 4° C. for 18-24 hours. Streptavidin-Aβ (Cat. No. 13043E, BD PharMingen, Franklin Lakes, N.J.) was diluted in the same media and added to washed plates; plates were incubated at room temperature and in the dark for two hours. Filtered 1-Step NBT/BCIP Substrate (Pierce, Rockford, Ill., Cat. No. 34042) was added and a further incubation at room temperature in the dark for ten minutes was performed. After washing, plates were allowed to dry before being imaged with a CCD camera and the spots within each well were automatically counted by computer.

Applicants have established that spot forming cells per million PBMCs (SFC/$10^6$ PBMCs) must exceed 55 and must exceed 4-fold the negative control to be defined as a positive result; failing to meet both these criteria defines a negative result. Rhesus macaques were vaccinated with either a MAP construct comprising Aβ (3-10)/(21-28) (Construct No. 12, FIG. 6A) conjugated to OMPC or with both of two monomeric constructs, Aβ (3-10) (SEQ ID NO: 69) and Aβ (21-28) (SEQ ID NO: 73) conjugated to OMPC. Each macaque was assayed during the vaccination regimen at monthly intervals for three or four months; the highest signal ever recorded against either Aβ 1-40 or Aβ 1-20 is only 18 SFC/$10^6$ PBMCs, significantly below the 55 SFC/$10^6$ PBMCs criterion. Thus, all resulted in a negative score, providing strong evidence that the vaccines did not elicit T-cell responses and, as such, did not include a T-cell epitope.

Example 6

Elevation of Plasma Aβ

Rhesus macaque non-human primates (N=3) were immunized with 5 µg of the MAP Aβ (3-10)/(21-28) conjugate (Construct No. 12, FIG. 6A) or its monomeric constituent conjugate, Aβ (3-10) (SEQ ID NO: 69) and Aβ (21-28) (SEQ ID NO: 73) linked to OMPC as the carrier and formulated in MAA plus 100 µg ISCOMATRIX®. The rhesus primates received vaccinations every four weeks with bleeds collected and analyzed four weeks following each injection. Anti-Aβ$_{40}$ titers and total Aβ$_{1-40}$ levels were determined.

Plasma Aβ$_{1-40}$ levels were determined in these immunized animals using a 6E10/G210 ELISA. This assay measures Aβ$_{1-40}$ using a sandwich ELISA comprising an N-terminal capture antibody 6E10 (Aβ 1-8) (Signet Laboratories, Dedham, Mass.) and a C-terminal Aβ$_{40}$ neo-epitope antibody (G210) (The Genetics Company, Inc., Zurich, Switzerland) conjugated with alkaline phosphatase. The antibody, 6E10, was coated onto plates at a concentration of 5 ug/ml. Diluted plasma samples (1:3) were used at 50 µl/well in triplicates. Aβ$_{1-40}$ standards were prepared from 400 pM-3 pM in 6E10 immuno-depleted rhesus plasma matrix. This assay has a signal-to-noise ratio of about 5-20. The CDP-star alkaline phosphatase substrate was obtained from Applied Biosystems, Foster City, Calif. SuperBlock®, a pre-formulated blocking buffer, was obtained from Pierce Biotechnology, Rockford, Ill. (Cat#37515). Counts from individual samples, run in triplicate, were converted to actual analyte concentrations using a third order spline fit to the standards. QC samples were run to evaluate plate to plate variability of the signal.

Figure 8A:
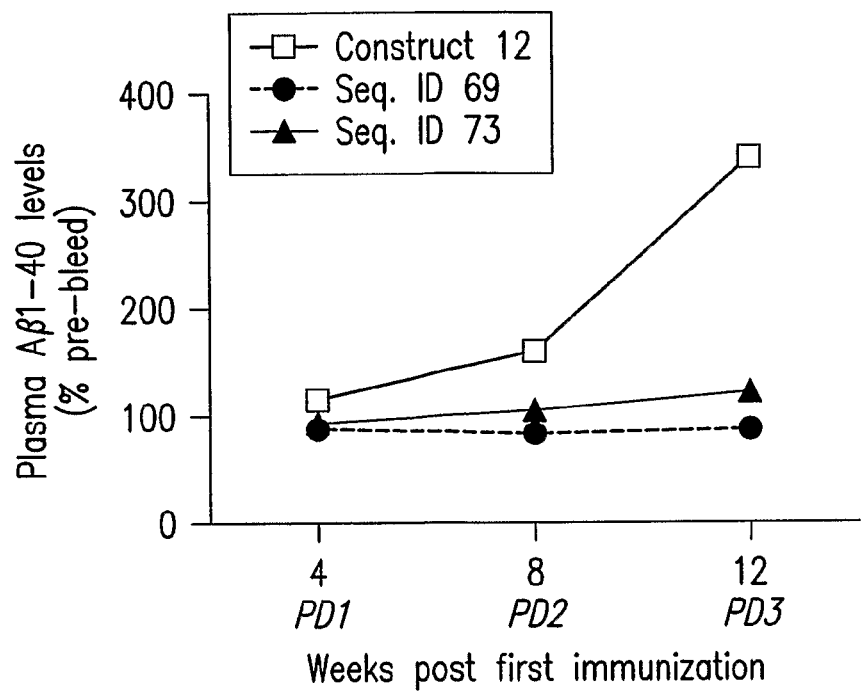
FIG. 8A shows a greater than three-fold elevation following administration of a MAP construct comprising Aβ (3-10)/(21-28) (Construct No. 12, FIG. 6A) conjugated to OMPC versus the monomeric constructs, Aβ (3-10) (SEQ ID NO: 69) and Aβ (21-28) (SEQ ID NO: 73) (□, Construct No. 12, FIG. 6A; ●, Aβ (3-10) (SEQ ID NO 69), ▲, Aβ (21-28) (SEQ ID NO: 73).
Figure 8B:
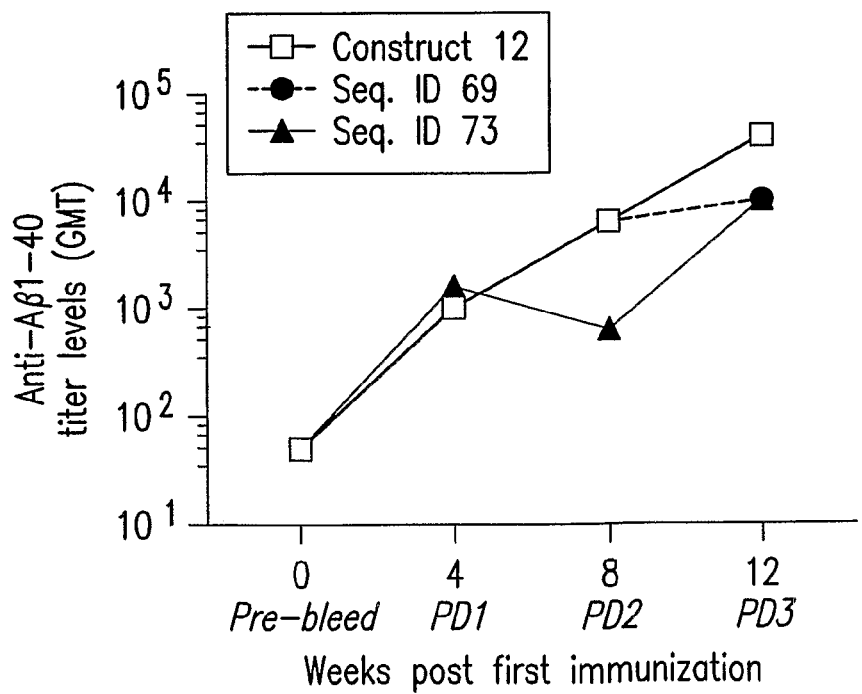
FIG. 8B shows that plasma Aβ levels are independent of titer levels (□, Construct No. 12, FIG. 6A; ●, Aβ (3-10) (SEQ ID NO 69), ▲, Aβ (21-28) (SEQ ID NO: 73).

As depicted in FIG. 8A, the results of these analyses demonstrated a greater than 3-fold increase in plasma Aβ$_{40}$ at PD3 following immunization with the MAP Aβ (3-10)/(21-28) construct (Construct No. 12, FIG. 6A). This increase in plasma Aβ$_{40}$ was not observed in animals immunized with the monomeric Aβ conjugate/OMPC vaccine constructs. Specifically, immunization using either Aβ (3-10) (SEQ ID NO: 69) or Aβ (21-28) (SEQ ID NO: 73) produced a lack of, or appreciably lower, response on this measure. It was notable that these differences were independent of titer levels as depicted in FIG. 8B.

Collectively, these data demonstrate that some constructs have an advantage relative to other immunogenic constructs with respect to their ability to elevate plasma Aβ levels. Those skilled in the art would appreciate that this selectivity of immunogenic fragments, i.e. the ability to elevate plasma Aβ levels, has not been shown prior to the invention herein and was not predictable from the prior art. As such, the identification of immunogens, either 8-mers or MAPs, lacking a T-cell epitope, that elevate plasma Aβ following immunization, provides a method for selecting said 8-mers or MAPs for use in a vaccine construct. As a result of the invention herein, those skilled in the art are now able to characterize said vaccine constructs both quantitatively (i.e., immunogenicity) and qualitatively (i.e., nature of the polyclonal antibody response—ability to elevate plasma AB levels). It will be further appreciated by those skilled in the art that the invention herein is not limited to 8-amino acid Aβ fragments, but is inclusive of any antigen capable of producing a polyclonal antibody response in the host organism that is reactive to Aβ.

What is claimed:

1. A composition comprising a multivalent branched multiple antigen peptide (MAP) linked to a carrier to form a conjugate, wherein the MAP comprises two or more non-identical immunogenic linear 8 amino acid peptide fragments (8-mers) of Aβ, each fragment lacking a T-cell epitope, and wherein one of said 8-mers is Aβ 21-28 (AEDVGSNK) (SEQ ID NO: 22).

2. The composition of claim 1 wherein one of the immunogenic fragments of Aβ is selected from the group consisting of an 8-mer corresponding to amino acid regions Aβ 1-8, Aβ 2-9, Aβ 3-10, Aβ 7-14, Aβ 17-24, and Aβ 33-40.

3. The composition of claim 1 wherein the MAP is selected from the group consisting of amino acid regions a) A⊕1-8 and Aβ21-28, b) Aβ 3-10 and Aβ 21-28, c) Aβ 7-14 and Aβ 21-28 and Aβ 3-10, and d) Aβ 7-14 and Aβ 33-40 and Aβ 21-28 and Aβ 3-10, wherein each of the 8-mers are linked together.

4. The composition of claim 3 wherein the MAP comprises the 8-mers Aβ 3-10 and Aβ 21-28 linked together on a lysine-based scaffold.

5. The composition of claim 1 wherein the carrier is selected from the group consisting of serum albumin, keyhole limpet hemocyanin (KLH), an immunoglobulin, a tetanus toxoid protein, a bacterial toxoid protein, and an attenuated toxin derivative.

6. The composition of claim 4 wherein the carrier is the outer membrane protein complex of *Neisseria meningitidis* (OMPC).

7. A pharmaceutical composition comprising the composition of claim 1 and a pharmaceutically acceptable adjuvant.

8. The pharmaceutical composition of claim 7 wherein the pharmaceutically acceptable adjuvant is selected from the group consisting of an aluminum salt, alum, a lipid, and a saponin-based adjuvant.

9. A pharmaceutical composition comprising the composition of claim 6 and a saponin-based adjuvant.

10. A pharmaceutical composition comprising a MAP linked to a carrier to form a conjugate, wherein the MAP comprises the 8-mers Aβ 3-10 and Aβ 21-28 linked together on a lysine-based scaffold and the carrier is OMPC, and a saponin-based adjuvant.

* * * * *